US010555912B2

(12) United States Patent
Foss et al.

(10) Patent No.: US 10,555,912 B2
(45) Date of Patent: *Feb. 11, 2020

(54) USE OF POLYMERIC EXCIPIENTS FOR LYOPHILIZATION OR FREEZING OF PARTICLES

(71) Applicant: Abraxis BioScience, LLC, Summit, NJ (US)

(72) Inventors: Willard Foss, San Diego, CA (US); Rajesh Shinde, Waltham, MA (US)

(73) Assignee: Abraxis BioScience, LLC, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/107,419

(22) Filed: Aug. 21, 2018

(65) Prior Publication Data

US 2019/0054033 A1    Feb. 21, 2019

Related U.S. Application Data

(63) Continuation of application No. 15/412,897, filed on Jan. 23, 2017, now Pat. No. 10,076,501, which is a continuation of application No. 14/362,382, filed as application No. PCT/US2012/069585 on Dec. 13, 2012, now Pat. No. 9,585,960.

(60) Provisional application No. 61/570,735, filed on Dec. 14, 2011.

(51) Int. Cl.
| | |
|---|---|
| *A61K 9/19* | (2006.01) |
| *A61K 9/51* | (2006.01) |
| *A61K 31/337* | (2006.01) |
| *A61K 9/00* | (2006.01) |
| *A61K 9/10* | (2006.01) |
| *A61P 35/00* | (2006.01) |
| *A61K 9/127* | (2006.01) |
| *A61K 9/107* | (2006.01) |
| *A61K 47/32* | (2006.01) |
| *A61K 9/50* | (2006.01) |
| *A61K 47/26* | (2006.01) |

(52) U.S. Cl.
CPC .......... *A61K 9/5138* (2013.01); *A61K 9/0019* (2013.01); *A61K 9/10* (2013.01); *A61K 9/107* (2013.01); *A61K 9/1271* (2013.01); *A61K 9/19* (2013.01); *A61K 9/5031* (2013.01); *A61K 9/5089* (2013.01); *A61K 9/5123* (2013.01); *A61K 9/5146* (2013.01); *A61K 9/5153* (2013.01); *A61K 9/5192* (2013.01); *A61K 31/337* (2013.01); *A61K 47/26* (2013.01); *A61K 47/32* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,362,478 A | 11/1994 | Desai et al. | |
| 5,439,686 A | 8/1995 | Desai et al. | |
| 5,498,421 A | 3/1996 | Grinstaff et al. | |
| 5,505,932 A | 4/1996 | Grinstaff et al. | |
| 5,508,021 A | 4/1996 | Grinstaff et al. | |
| 5,512,268 A | 4/1996 | Grinstaff et al. | |
| 5,560,933 A | 10/1996 | Soon-Shiong et al. | |
| 5,635,207 A | 6/1997 | Grinstaff et al. | |
| 5,639,473 A | 6/1997 | Grinstaff et al. | |
| 5,650,156 A | 7/1997 | Grinstaff et al. | |
| 5,665,382 A | 9/1997 | Grinstaff et al. | |
| 5,665,383 A | 9/1997 | Grinstaff et al. | |
| 5,916,596 A | 6/1999 | Desai et al. | |
| 5,997,904 A | 12/1999 | Magdassi et al. | |
| 6,096,331 A | 8/2000 | Desai et al. | |
| 6,284,280 B1 | 9/2001 | Weitschies et al. | |
| 6,391,224 B1 * | 5/2002 | Wowk | A01N 1/02 106/13 |
| 6,506,405 B1 | 1/2003 | Desai et al. | |
| 6,528,067 B1 | 3/2003 | Magdassi et al. | |
| 6,537,579 B1 | 3/2003 | Desai et al. | |
| 6,565,842 B1 | 5/2003 | Desai et al. | |
| 6,652,884 B2 | 11/2003 | Falciani | |
| 6,749,868 B1 | 6/2004 | Desai et al. | |
| 6,753,006 B1 | 6/2004 | Desai et al. | |
| 7,368,129 B1 * | 5/2008 | Aneja | A61K 9/1271 264/4.1 |
| 7,758,891 B2 | 7/2010 | Desai et al. | |
| 7,771,751 B2 | 8/2010 | Desai et al. | |
| 7,780,984 B2 | 8/2010 | Desai et al. | |
| 7,820,788 B2 | 10/2010 | Desai et al. | |
| 7,923,536 B2 | 4/2011 | Desai et al. | |
| 7,981,445 B2 | 7/2011 | De et al. | |
| 8,034,375 B2 | 10/2011 | Desai et al. | |
| 8,034,765 B2 | 10/2011 | De et al. | |
| 8,137,684 B2 | 3/2012 | Desai et al. | |
| 8,138,229 B2 | 3/2012 | Desai et al. | |
| 8,257,733 B2 | 9/2012 | Desai et al. | |
| 8,268,348 B2 | 9/2012 | Desai et al. | |

(Continued)

FOREIGN PATENT DOCUMENTS

| | | |
|---|---|---|
| CN | 1 398 585 A | 2/2003 |
| EP | 1 151 748 A1 | 11/2001 |

(Continued)

OTHER PUBLICATIONS

Abdel-Mottaleb, M.M. A. et al.(2009). "Physically Cross-Linked Polyvinyl Alcohol for the Topical Delivery of Fluconazole," *Drug Development and Industrial Pharmacy* 35:311-320.

(Continued)

*Primary Examiner* — Robert A Wax
*Assistant Examiner* — Melissa S Mercier
(74) *Attorney, Agent, or Firm* — Morrison & Foerster LLP

(57) ABSTRACT

Provided herein are use of polymeric excipients, specifically polyvinyl alcohols, optionally in conjunction with sugars, as cryoprotectants to prevent aggregation of PEG-containing particles. Also provided are PEG-containing particles comprising such polymeric excipients.

46 Claims, No Drawings

(56) References Cited

U.S. PATENT DOCUMENTS

| | | | |
|---|---|---|---|
| 8,314,156 B2 | 11/2012 | Desai et al. | |
| 8,735,394 B2 | 5/2014 | Desai et al. | |
| 8,846,771 B2 | 9/2014 | Desai et al. | |
| 8,853,260 B2 | 10/2014 | Desai et al. | |
| 8,911,786 B2 | 12/2014 | Desai et al. | |
| 8,927,019 B2 | 1/2015 | Desai et al. | |
| 8,999,396 B2 | 4/2015 | Desai et al. | |
| 9,012,518 B2 | 4/2015 | Desai et al. | |
| 9,012,519 B2 | 4/2015 | Desai et al. | |
| 9,061,014 B2 | 6/2015 | Seward et al. | |
| 9,101,543 B2 | 8/2015 | Desai et al. | |
| 9,149,455 B2 | 10/2015 | Desai et al. | |
| 9,308,180 B2 | 4/2016 | De et al. | |
| 9,393,318 B2 | 7/2016 | Desai et al. | |
| 9,399,071 B2 | 7/2016 | Desai et al. | |
| 9,399,072 B2 | 7/2016 | Desai et al. | |
| 9,446,003 B2 | 9/2016 | Desai et al. | |
| 9,511,046 B2 | 12/2016 | Desai et al. | |
| 9,561,288 B2 | 2/2017 | Desai et al. | |
| 9,585,960 B2 * | 3/2017 | Foss | A61K 9/19 |
| 9,597,409 B2 | 3/2017 | Desai et al. | |
| 9,675,578 B2 | 6/2017 | Desai et al. | |
| 9,724,323 B2 | 8/2017 | Desai et al. | |
| 9,820,949 B2 | 11/2017 | Desai et al. | |
| 9,855,220 B2 | 1/2018 | Desai et al. | |
| 9,884,013 B2 | 2/2018 | Seward et al. | |
| 9,962,373 B2 | 5/2018 | Desai et al. | |
| 10,076,501 B2 * | 9/2018 | Foss | A61K 9/19 |
| 10,258,565 B2 | 4/2019 | Seward | |
| 2003/0185894 A1 | 10/2003 | Zenoni et al. | |
| 2003/0187062 A1 | 10/2003 | Zenoni et al. | |
| 2003/0199425 A1 | 10/2003 | Desai et al. | |
| 2004/0091546 A1 | 5/2004 | Johnson | |
| 2004/0115277 A1 | 6/2004 | Kissel | |
| 2005/0004002 A1 | 1/2005 | Desai et al. | |
| 2008/0280987 A1 | 11/2008 | Desai et al. | |
| 2009/0263483 A1 | 10/2009 | Desai et al. | |
| 2010/0034892 A1 | 2/2010 | Mao | |
| 2010/0048499 A1 | 2/2010 | Desai et al. | |
| 2010/0166869 A1 | 7/2010 | Desai et al. | |
| 2010/0297243 A1 | 11/2010 | Desai et al. | |
| 2011/0052708 A1 | 3/2011 | Soon-Shiong et al. | |
| 2011/0118342 A1 | 5/2011 | De et al. | |
| 2011/0151012 A1 | 6/2011 | Desai et al. | |
| 2011/0196026 A1 | 8/2011 | De et al. | |
| 2011/0237686 A1 | 9/2011 | Ng et al. | |
| 2011/0275704 A1 | 11/2011 | Troiano et al. | |
| 2012/0070502 A1 | 3/2012 | Desai et al. | |
| 2012/0076862 A1 | 3/2012 | Desai et al. | |
| 2012/0128732 A1 | 5/2012 | Trieu et al. | |
| 2012/0189701 A1 | 7/2012 | Desai et al. | |
| 2012/0225129 A1 * | 9/2012 | Eliasof | C12N 15/87 424/499 |
| 2012/0231082 A1 | 9/2012 | Desai et al. | |
| 2012/0283205 A1 | 11/2012 | Desai et al. | |
| 2012/0308612 A1 | 12/2012 | De et al. | |
| 2013/0045240 A1 | 2/2013 | Tao et al. | |
| 2013/0071438 A1 | 3/2013 | Desai et al. | |
| 2013/0115296 A1 | 5/2013 | Yeo et al. | |
| 2013/0195922 A1 | 8/2013 | Desai et al. | |
| 2013/0195983 A1 | 8/2013 | Desai et al. | |
| 2013/0195984 A1 | 8/2013 | Desai et al. | |
| 2013/0202709 A1 | 8/2013 | Desai et al. | |
| 2013/0209518 A1 | 8/2013 | Desai et al. | |
| 2013/0244952 A1 | 9/2013 | Desai et al. | |
| 2013/0266659 A1 | 10/2013 | Desai et al. | |
| 2013/0280336 A1 | 10/2013 | Desai et al. | |
| 2013/0280337 A1 | 10/2013 | Desai et al. | |
| 2014/0017315 A1 | 1/2014 | Desai et al. | |
| 2014/0017316 A1 | 1/2014 | Desai et al. | |
| 2014/0017323 A1 | 1/2014 | Desai et al. | |
| 2014/0023717 A1 | 1/2014 | Desai et al. | |
| 2014/0039069 A1 | 2/2014 | Desai et al. | |
| 2014/0039070 A1 | 2/2014 | Desai et al. | |
| 2014/0056986 A1 | 2/2014 | Desai et al. | |
| 2014/0072630 A1 | 3/2014 | Tao et al. | |
| 2014/0072631 A1 | 3/2014 | Trieu et al. | |
| 2014/0072643 A1 | 3/2014 | Desai et al. | |
| 2014/0079787 A1 | 3/2014 | Yeo et al. | |
| 2014/0079788 A1 | 3/2014 | Desai et al. | |
| 2014/0079793 A1 | 3/2014 | Desai et al. | |
| 2014/0080901 A1 | 3/2014 | Desai et al. | |
| 2014/0134257 A1 | 5/2014 | Desai et al. | |
| 2014/0155344 A1 | 6/2014 | Desai et al. | |
| 2014/0170228 A1 | 6/2014 | Desai et al. | |
| 2014/0186447 A1 | 7/2014 | Desai | |
| 2014/0199403 A1 | 7/2014 | Desai et al. | |
| 2014/0199404 A1 | 7/2014 | Heise et al. | |
| 2014/0199405 A1 | 7/2014 | Pierce et al. | |
| 2014/0271871 A1 | 9/2014 | Desai et al. | |
| 2014/0296279 A1 | 10/2014 | Seward et al. | |
| 2014/0296353 A1 | 10/2014 | Desai et al. | |
| 2014/0302157 A1 | 10/2014 | Desai et al. | |
| 2015/0050356 A1 | 2/2015 | Desai et al. | |
| 2015/0079177 A1 | 3/2015 | Desai et al. | |
| 2015/0079181 A1 | 3/2015 | Desai et al. | |
| 2015/0104521 A1 | 4/2015 | Desai et al. | |
| 2015/0111960 A1 | 4/2015 | Desai et al. | |
| 2015/0165047 A1 | 6/2015 | Desai et al. | |
| 2015/0190519 A1 | 7/2015 | Desai et al. | |
| 2015/0313866 A1 | 11/2015 | Desai et al. | |
| 2016/0008330 A1 | 1/2016 | Desai et al. | |
| 2016/0015681 A1 | 1/2016 | Desai et al. | |
| 2016/0015817 A1 | 1/2016 | Benettaib et al. | |
| 2016/0151325 A1 | 6/2016 | Desai et al. | |
| 2016/0228401 A1 | 8/2016 | Desai et al. | |
| 2016/0374952 A1 | 12/2016 | Yeo et al. | |
| 2017/0007569 A1 | 1/2017 | De et al. | |
| 2017/0014373 A1 | 1/2017 | Desai et al. | |
| 2017/0020824 A1 | 1/2017 | Desai et al. | |
| 2017/0049711 A1 | 2/2017 | Desai et al. | |
| 2017/0100344 A1 | 4/2017 | Desai et al. | |
| 2017/0105951 A1 | 4/2017 | Desai et al. | |
| 2017/0157035 A1 | 6/2017 | Seward et al. | |
| 2017/0172975 A1 | 6/2017 | Desai et al. | |
| 2017/0181988 A1 | 6/2017 | Desai et al. | |
| 2017/0202782 A1 | 7/2017 | Pierce et al. | |
| 2017/0224627 A1 | 8/2017 | Foss et al. | |
| 2017/0333384 A1 | 11/2017 | Desai et al. | |
| 2017/0340599 A1 | 11/2017 | Desai et al. | |
| 2018/0015181 A1 | 1/2018 | Desai et al. | |
| 2018/0064679 A1 | 3/2018 | Pierce et al. | |
| 2018/0133157 A1 | 5/2018 | Desai et al. | |
| 2018/0147139 A1 | 5/2018 | Seward et al. | |
| 2018/0153820 A1 | 6/2018 | Desai et al. | |
| 2018/0153863 A1 | 6/2018 | Desai et al. | |
| 2018/0169017 A1 | 6/2018 | Desai et al. | |
| 2018/0177770 A1 | 6/2018 | Desai et al. | |
| 2018/0177771 A1 | 6/2018 | Desai et al. | |
| 2018/0214425 A1 | 8/2018 | Desai et al. | |
| 2018/0256551 A1 | 9/2018 | Desai et al. | |
| 2018/0289620 A1 | 10/2018 | Desai et al. | |
| 2018/0374583 A1 | 12/2018 | Goldstein et al. | |
| 2019/0022020 A1 | 1/2019 | Desai et al. | |
| 2019/0054033 A1 | 2/2019 | Foss et al. | |
| 2019/0147986 A1 | 5/2019 | Luo | |
| 2019/0167629 A1 | 6/2019 | Desai | |
| 2019/0175564 A1 | 6/2019 | Desai | |
| 2019/0183789 A1 | 6/2019 | Seward | |
| 2019/0184031 A1 | 6/2019 | Desai | |
| 2019/0192477 A1 | 6/2019 | Desai | |
| 2019/0247357 A1 | 8/2019 | Foss | |

FOREIGN PATENT DOCUMENTS

| | | |
|---|---|---|
| JP | 2003-12505 A | 1/2003 |
| JP | 2005-213170 A | 8/2005 |
| JP | 2006-321763 A | 11/2006 |
| RU | 2291686 C2 | 1/2007 |
| WO | WO-1994/18954 A1 | 9/1994 |
| WO | WO-1998/14174 A1 | 4/1998 |
| WO | WO-1998/14175 A1 | 4/1998 |
| WO | WO-1999/00113 A1 | 1/1999 |
| WO | WO-2000/040259 A1 | 7/2000 |

(56) References Cited

FOREIGN PATENT DOCUMENTS

| | | |
|---|---|---|
| WO | WO-2000/64437 A1 | 11/2000 |
| WO | WO-2000/71079 A2 | 11/2000 |
| WO | WO-2000/71079 A3 | 11/2000 |
| WO | WO-2001/89522 A1 | 11/2001 |
| WO | WO-2002/087545 A1 | 11/2002 |
| WO | WO-2003/096944 A1 | 11/2003 |
| WO | WO-2004/052401 A2 | 6/2004 |
| WO | WO-2004/052401 A3 | 6/2004 |
| WO | WO-2006/089290 A1 | 8/2004 |
| WO | WO-2005/072707 A1 | 8/2005 |
| WO | WO-2007/027819 A2 | 3/2007 |
| WO | WO-2007/027819 A3 | 3/2007 |
| WO | WO-2007/027941 A2 | 3/2007 |
| WO | WO-2007/027941 A3 | 3/2007 |
| WO | WO-2008/027055 A1 | 3/2008 |
| WO | WO-2008/057562 A1 | 5/2008 |
| WO | WO-2008/076373 A1 | 6/2008 |
| WO | WO-2008/109163 A1 | 9/2008 |
| WO | WO-2008/137148 A2 | 11/2008 |
| WO | WO-2008/137148 A3 | 11/2008 |
| WO | WO 2008/150532 A1 | 12/2008 |
| WO | WO 2009/126175 A1 | 10/2009 |
| WO | WO 2009/126401 A1 | 10/2009 |
| WO | WO 2009/126938 A1 | 10/2009 |
| WO | WO 2010/068899 | 6/2010 |
| WO | WO-2010/068925 A1 | 6/2010 |
| WO | WO-2010/105172 A1 | 9/2010 |
| WO | WO 2010/118365 A1 | 10/2010 |
| WO | WO 2010/121000 A1 | 10/2010 |
| WO | WO-2011/025838 A1 | 3/2011 |
| WO | WO-2011/072218 A2 | 6/2011 |
| WO | WO-2011/119988 A1 | 9/2011 |
| WO | WO-2011/123393 A1 | 10/2011 |
| WO | WO-2011/123395 A1 | 10/2011 |
| WO | WO-2011/153009 A1 | 12/2011 |
| WO | WO-2011/153010 A1 | 12/2011 |
| WO | WO-2011/156119 A1 | 12/2011 |
| WO | WO-2012/149451 A1 | 11/2012 |
| WO | WO-2013/090634 A1 | 6/2013 |
| WO | WO-2014/110345 A1 | 7/2014 |
| WO | WO-2014/110408 A1 | 7/2014 |
| WO | WO-2014/110443 A1 | 7/2014 |
| WO | WO-2014/123612 A1 | 8/2014 |
| WO | WO-2014/143613 A1 | 9/2014 |
| WO | WO-2014/151853 A1 | 9/2014 |
| WO | WO-2014/159171 A1 | 10/2014 |

OTHER PUBLICATIONS

Abdelwahed, W. et al. (Dec. 30, 2006, e-pub. Oct. 6, 2006). "Freeze-Drying of Nanoparticles: Formulation, Process and Storage Consideration," *Advanced Drug Delivery Reviews* 58(15):1688-1713.

Abdelwahed W, et al. (2006, Dec. 2, 2005). "A Pilot Study of Freeze Drying of Poly(Epsilon-Caprolactone) Nanocapsules Stabilized by Poly(Vinyl Alcohol): Formulation and Process Optimization," *International Journal of Pharmaceutics* 309:178-188.

Allen, T.M. et al. (1991). "Pharmacokinetic of Stealth Versus Conventional Liposomes: Effect of Dose," *Biochimica et Biophysica Acta* 1068:133-141.

Belikov, V.G. (1993). *Farmatsevticheskaya Khimiya (Pharmaceutical Chemistry)*. In 2 parts. Part 1: General Pharmaceutical Chemistry. M.: Vysshaya shkola., 8.2-8.3, pp. 388-389, three pages total. (English Translation).

Bhardwaj, U. et al. (Jan. 2007). "Controlling Acute Inflammation with Fast Releasing Dexamethasone-PLGA Microsphere/PVA Hydrogel Composites for Implantable Devices," *Journal of Diabetes Science and Technology* 1(1):8-17.

Chen, W. et al. (2011, e-pub. Jul. 22, 2011). "Suitable Carriers for Encapsulation and Distribution of Endostar: Comparison of Endostar-Loaded Particulate Carriers," *Int. J. Nanomedicine* 6:1535-1541.

Chueshov, V.I. (2002). *Promyshlennaya Tekhnologiya Lekarstv, Drug Manufacturing Technologies*, vol. 1, Kharkov, NFAU Publishers, pp. 24-25, English Translation, 2 pages, with translation certification, (Total pages 6).

Da Silva, A.R. et al. (2010). "Drug Release From Microspheres and Nanospheres of Poly(lactide-co-glycolide) Without Sphere Separation From the Release Medium," *J. Braz. Chem. Soc.* 21(2):214-225.

De Jaeghere, F. et al. (Jun. 1999). "Formulation and Lyophilization of Poly(Lactic Acid-Co-Ethylene Oxide) Particles: Influence on Physical Stability and In Vitro Cell Uptake," *Pharmaceutical Research* 16(6):859-866.

Gref, R. et al. (Mar. 18, 1994). "Biodegradable Long-Circulating Polymeric Nanospheres," *Science* 263:1600-1603.

Gupta, R.B. et al. (Apr. 2011). "Polymeric Nanoparticles for Oral Drug Delivery," in *Nanoparticle Technology for Drug Delivery*, Science Press, the first edition, p. 145. (English Translation of p. 145).

Kreuter, J. (Jul.-Aug. 1991). "Peroral Administration of Nanoparticles," *Adv. Drug Del. Rev.* 7(1):71-86.

Ma, G. et al. (Mar. 2003). *New materials and Applied Technology: New Polymer Materials*, Chemical industry press, $1^{st}$ edition, p. 155, (English Translation of paragraph 2 relevant section).

Mosquiera, V.C.F. et al. (2001). "Relationship Between Complement Activation, Cellular Uptake and Surface Physicochemical Aspects of Novel PEG-Modified Nanocapsules," *Biomaterials* 22:2967-2979.

Müller, B.G. et al. (1996). "Albumin Nanoparticles as Carriers for Passive Drug Targeting: An Optimized Manufacturing Technique," *Pharmaceutical Research* 13(1):32-37.

Sahoo, S.K. et al. (2002). "Residual Polyvinyl Alcohol Associated With Poly(D,L-lactide-co-glycolide) Nanoparticles Affects Their Physical Properties and Cellular Uptake," *Journal of Controlled Release* 82:105-114.

Stolnik et al. (1994). "Surface Modification of Poly(lactide-co-glycolide) Nanospheres by Biodegradable Poly(lactide)-Poly(Ethylene Glycol) Copolymers," *Pharm. Res.* 11:1800-1808.

Vauthier, C. et al. (May 2009). "Methods for the Preparation and Manufacture of Polymeric Particles," *Pharmaceutical Research* 26(5):1025-1058.

Verrecchia, T. et al. (1995). "Non-Stealth (Poly(Lactic Acid/Albumin)) and Stealth (Poly(Lactic Acid-Polyethylene Glycol)) Nanoparticles as Injectable Drug Carriers," *J. Controlled Rel*, 36:49-61.

Wendoff, J. et al. (Dec. 2006). "A Practical Approach to the use of Nanoparticles for Vaccine Delivery," *Journal of Pharmaceutical Sciences* 95(12):2738-2750.

Wu, L. et al. (2010). "Preparation and Characterization of Paclitaxel Delivery System Based on Semi-Solid Lipid Nanoparticles Coated With Poly(ethylene glycol)," *Pharmazie* 65:493-499.

Zimmer, A. et al. (1995). "Microspheres and Nanoparticles Used in Ocular Delivery Systems," *Adv. Drug Del. Rev.*, 16:61-73.

Extended European Search Report dated Apr. 10, 2015, for EP Application No. 12858155.0, filed on Dec. 13, 2012, 12 pages.

International Search Report dated Feb. 4, 2013, for PCT Application No. PCT/US2012/069585, filed on Dec. 13, 2012, four pages.

Written Opinion dated Feb. 4, 2013, for PCT Application No. PCT/US2012/069585, filed on Dec. 13, 2012, four pages.

U.S. Appl. No. 15/399,366, filed Jan. 5, 2017, for Pierce et al. (U.S. Patent Application is not submitted herewith pursuant to the waiver of 37 C.F.R. § 1.98(a)(2)(iii) issued by the Office on Sep. 21, 2004.).

U.S. Appl. No. 15/462,361, filed Mar. 17, 2017, for Tao et al. (U.S. Patent Application is not submitted herewith pursuant to the waiver of 37 C.F.R. § 1.98(a)(2)(iii) issued by the Office on Sep. 21, 2004.).

U.S. Appl. No. 15/663,351, filed Jul. 28, 2017, for Desai et al. (U.S. Patent Application is not submitted herewith pursuant to the waiver of 37 C.F.R. § 1.98(a)(2)(iii) issued by the Office on Sep. 21, 2004.).

U.S. Appl. No. 15/796,578, filed Oct. 27, 2017, for Desai et al. (U.S. Patent Application is not submitted herewith pursuant to the waiver of 37 C.F.R. § 1.98(a)(2)(iii) issued by the Office on Sep. 21, 2004.).

(56) References Cited

OTHER PUBLICATIONS

U.S. Appl. No. 16/101,027, filed Aug. 10, 2018, for Desai et al. (U.S. Patent Application is not submitted herewith pursuant to the waiver of 37 C.F.R. § 1.98(a)(2)(iii) issued by the Office on Sep. 21, 2004.).
U.S. Appl. No. 16/140,339, filed Sep. 24, 2018, for Desai et al. (U.S. Patent Application is not submitted herewith pursuant to the waiver of 37 C.F.R. § 1.98(a)(2)(iii) issued by the Office on Sep. 21, 2004.).
U.S. Appl. No. 16/170,522, filed Oct. 25, 2018, for Desai et al. (U.S. Patent Application is not submitted herewith pursuant to the waiver of 37 C.F.R. § 1.98(a)(2)(iii) issued by the Office on Sep. 21, 2004.).
Johnson, B.K. et al. (Sep. 2003). "Chemical Processing and Micromixing in Confined Impinging Jets," AIChE Journal 49(9):2264-2282.

\* cited by examiner

USE OF POLYMERIC EXCIPIENTS FOR LYOPHILIZATION OR FREEZING OF PARTICLES

RELATED APPLICATIONS

This application is a continuation of U.S. patent application Ser. No. 15/412,897, filed Jan. 23, 2017, which is a continuation of U.S. patent application Ser. No. 14/362,382 (now U.S. Pat. No. 9,585,960), which adopts the international filing date of Dec. 13, 2012, which is a National Phase application under 35 U.S.C. § 371 of International Application No. PCT/US2012/069585, filed Dec. 13, 2012, and claims priority benefit to provisional application No. 61/570,735 filed Dec. 14, 2011, the disclosures of each of which are incorporated herein by reference in their entirety.

TECHNICAL FIELD

This application pertains to compositions of pegylated-particles comprising drugs which are stable upon lyophilization or freezing.

BACKGROUND

The therapeutic effectiveness of many drugs is reduced by their lack of solubility in water and permeability into tissues. In recent years polymeric particles have emerged as attractive drug administration systems. Particles are used to encapsulate a variety of drugs for controlled delivery and improved solubilization. Because of their smaller size they generally exhibit greater intra-cellular uptake and are suitable for administration of drugs through various routes, such as orally, parenterally and oculary. (Kreuter, *Adv. Drug Del. Rev.*, 7.71-86 (1991); Gref et al., *Science*, 263:1600-1603 (1994); Zimmer and Kreuter, *Adv. Drug Del. Rev.*, 16:61-73 (1995)). The controlled release of drugs allows prolonging the effect of molecules with low biological half-lives, prevents over-dosage and lowers toxic side effects. Moreover, by incorporating molecules with different physico-chemical features, these carriers can be modified to achieve variable release rates or to target specific organs or cells.

Despite their potential advantages, conventional particles have significant drawbacks with respect to their use in drug administration. Their instability in gastrointestinal fluids, a low degree of intestinal absorption, and non-specific adhesion, reduce their utility in oral administration. Parenteral administration can overcome some of these problems by specifically targeting drugs to certain organs. However, particles are quickly recognized, taken up and eliminated from the blood circulation by macrophages of the mononuclear phagocyte system (MPS) after their intravenous administration. This phenomenon limits their function in controlled release and reduces their effective concentration in the tissues.

Modification of the characteristics of the polymeric matrix and the surface of the particles may provide solution to some of the problems described above. One possible modification is pegylation or attaching polyethylene glycol (PEG) to particles. The association of polyethylene glycols to particles protects them from enzymatic attacks in digestive fluids. PEG coated particles have demonstrated prolonged circulation and longer plasma half-life. (Gref et al., *Science*, 263:1600-1603 (1094); Stolnik et al., *Pharm. Res.*, 11:1800-1808 (1994); Verrecchia et al., *J. Controlled Rel.*, 36:49-61(1995)). The flexible and hydrophilic PEG chains apparently provide a steric stabilization that reduces protein interaction and uptake by macrophages. (T. M. Allen et al., *Biochimica et Biophysica Acta*, 1068: 133-141 (1991); Mosquiera et al., *Biomaterials*, 22:2967-2979 (2001))

However, physical instability (aggregation) and/or chemical instability (hydrolysis) have been observed when these particles are stored for extended period. Also, aqueous formulations containing protein are susceptible to microbial contamination because proteins are good substrates for microbial growth. In order to circumvent these problems, water has to be removed from these systems. Thus, injectable particles are preferably stored as dry powder in order to ensure ease of handling and transportation. A commonly used process that converts solutions or suspensions into solids is freeze-drying or lyophilization. It involves removing water from a frozen sample by sublimation and desorption under vacuum. A significant challenge encountered during the formation of such solid dried forms of particles is the difficulty in reconstituting the particles to their original size. Another commonly used process that converts solutions or suspensions into solids is freezing. Frozen suspensions also present a similar challenge in recovering particles to their original size upon thawing. The presence of PEG chains causes the individual particles to aggregate via entanglement and subsequent crystallization of the PEG chains during the freeze-dry cycle. However, for an intravenous administration of particles a mean particle size of 100-200 nm and a homogenous size distribution is needed to avoid the risk of embolism and to enable sterile filtration.

All references cited herein, including patent applications and publications, are incorporated by reference in their entirety.

SUMMARY OF THE INVENTION

The present invention in one aspect provides a method of preparing a lyophilized or frozen preparation of a composition comprising particles comprising a drug, wherein the particles comprise (such as coated with) PEG, the method comprising adding PVA to an aqueous composition comprising the particles and lyophilizing or freezing the aqueous composition. In some embodiments, there is provided a method of preventing particle aggregation and/or particle size increase upon lyophilization and resuspension or freezing and thawing of an aqueous composition comprising particles comprising a drug, wherein the particles comprise (such as coated with) PEG, the method comprising adding PVA to the aqueous particle composition prior to lyophilization or freezing.

In some embodiments according to any of the methods described above, the concentration of PVA in the aqueous particle composition is between about 0.05% (w/v) to about 1% (w/v), including for example about 0.1 to about 0.3%. In some embodiments according to any of the methods described above, the PVA is about 3K to about 125K, including for example about 13K or about 31 K. In some embodiments according to any of the methods described above, the PVA is at least about 50% hydrolyzed, for example at least about 75% hydrolyzed. In some embodiments according to any of the methods described above, the weight ratio of the PVA to the particles in the resultant composition is less than about 0.2:1. In some embodiments according to any of the methods described above, the concentration of the particles in the aqueous particle composition is about 1% to about 25% (w/v). In some embodiments according to any of the methods described above, the particles comprise a polymeric core matrix coated with PEG. In some embodiments, the particles comprise PLA or PLGA.

In some embodiments according to any of the methods described above, the average particle size of the particles in the particle composition is no greater than about 200 nm. In some embodiments according to any one of the methods described above, the PEG is covalently attached to the surface of the particles. In some embodiments, the PEG is tethered to the surface of the particles by hydrophobic or charge interactions. In some embodiments, the PEG is one of the structural components of the particles (for example, the particles can comprise PEG-PLGA or PEG-PLA co-blocks).

In some embodiments according to any of the methods described above, the average size of the particles does not change by more than about 10% upon lyophilization and resuspension or freezing and thawing. In some embodiments according to any one of the methods described above, the aqueous particle composition to which the PVA is added is substantially free (such as free) of PVA prior to the addition of the PVA.

In some embodiments according to any of the methods described above, the method further comprises adding a sugar (such as sucrose) to the aqueous particle composition prior to lyophilization or freezing. In some embodiments, the concentration of sucrose in the aqueous particle composition is between about 5% to about 20%. In some embodiments, the sugar (such as sucrose) and the PVA are added simultaneously to the particle composition. In some embodiments, the sugar (such as sucrose) and the PVA are added sequentially into the particle composition.

In another aspect, there are provided pharmaceutical compositions produced by any one of the methods described above. In some embodiments, there is provided a pharmaceutical composition comprising particles comprising a drug, wherein the particles comprise (such as coated with) PEG, wherein the composition further comprises PVA, and wherein less than about 2% of the total PVA in the pharmaceutical composition is associated with the particles. In some embodiments, the composition is lyophilized. In some embodiments, the composition is an aqueous suspension resuspended from a lyophilized composition. In some embodiments, the composition is an aqueous suspension. In some embodiments, the composition is a frozen composition. In some embodiments, the composition is thawed from a frozen composition. In some embodiments, the molecular weight of the PEG is at least about any of 2 kDa, 3 kDa, 5 kDa, 6 kDa, or 8 kDa. In some embodiments, the weight ratio of PEG to the particles is at least about 20%, 30%, 40%, 50%, 60%, or 70%.

In some embodiments according to any of the pharmaceutical compositions described above, the concentration of PVA in the aqueous particle composition is between about 0.05% to about 1%, including for example between about 0.1% to about 0.3%. In some embodiments according to any of the pharmaceutical compositions described above, the PVA is about 3 to about 125K, including for example about 13K or about 31 K. In some embodiments according to any of the pharmaceutical compositions described above, the PVA is at least about 50% hydrolyzed, including for example at least about 75% hydrolyzed.

In some embodiments according to any one of the pharmaceutical compositions described above, the particles comprise a polymeric matrix core coated with PEG. In some embodiments according to any of the pharmaceutical compositions described above, the particles comprise PLA or PLGA. In some embodiments according to any one of the pharmaceutical compositions described above, the average particle size of the particles in the particle composition is no greater than about 200 nm. In some embodiments, the PEG is covalently attached to the surface of the particles. In some embodiments, the PEG is tethered to the surface of the particles by hydrophobic or charge interactions. In some embodiments, the PEG is a structural component of the particle (for example, the particles can comprise PEG-PLGA or PEG-PLA co-blocks).

In some embodiments according to any one of the pharmaceutical compositions described above, the composition further comprises a sugar. In some embodiments, the sugar is sucrose. In some embodiments, the concentration of sucrose in the particle composition is between about 5% to about 20%.

In some embodiments according to any one of the pharmaceutical compositions described above, the weight ratio of the PVA the particles in the composition is less than about 0.2:1. In some embodiments according to any one of the pharmaceutical compositions described above, the concentration of the particles in the aqueous particle composition is about 1% to about 25% (w/v).

In some embodiments according to any one of the pharmaceutical compositions described above, the pharmaceutical composition is contained in a sealed vial.

It is to be understood that one, some, or all of the properties of the various embodiments described herein may be combined to form other embodiments of the present invention. These and other aspects of the invention will become apparent to one of skill in the art.

DETAILED DESCRIPTION

Provided herein are methods of preparing formulations or drugs contained in particles comprising (such as coated with) polyethylene glycol (PEG), such formulations having reduced particle aggregation and/or particle size change upon lyophilization freezing. The method comprises adding polyvinyl alcohol (PVA) to an aqueous composition of PEG-containing drug particles before the lyophilization or freezing process. The method may further comprise adding sugar (such as sucrose) to the aqueous suspension. Although PVA has been used previously as a stabilizer during the process of making particles, it has not been used previously in the same manner as the present invention, where PVA is added after the PEG-containing particles are fully formed. It was surprisingly found that, when PVA was added after the particles are fully formed, it can act a cryoprotectant and prevent the PEG-containing particle from aggregating and/or undergoing size changes.

The present invention thus in one aspect provides a method of preparing a (or frozen) preparation of a composition comprising particles comprising a drug, wherein the particles comprise (such as coated with) PEG, the method comprising adding PVA to an aqueous composition comprising the particles and lyophiling (or freezing) the aqueous composition. In some embodiments, there is provided a method of preventing particle aggregation and/or particle size increase upon lyophilization and resuspension (or freezing and thawing) of an aqueous composition comprising particles composing a drug, wherein the particles comprise (such as coated with) PEG, the method comprising adding PVA to the aqueous particle composition prior to lyophilization or freezing.

In another aspect, there is provided a pharmaceutical composition prepared by the methods described herein. In some embodiments, there is provided a pharmaceutical composition comprising particles comprising a drug, wherein the particles comprise (such as coated with) PEG, wherein the composition further comprises PVA, and wherein less than about 2% of the total PVA in the pharmaceutical composition is associated with the particles.

Methods of the Present Invention

The present invention provides a method of preparing a lyophilized (or frozen) preparation of a composition comprising particles (such as particles having an average diameter of no greater than about 200 nm) comprising a drug, wherein the particles comprise (such as coated with) PEG, the method comprising adding PVA to an aqueous composition comprising the particles and lyophilizing (or freezing,) the aqueous composition. In some embodiments, there is provided a method of preparing a lyophilized or frozen preparation of a composition comprising particles (such as particles having an average diameter of no greater than about 200 nm) comprising a drug, wherein the particles comprise (such as coated with) PEG, the method comprising adding PVA to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%. In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA to an aqueous composition comprising the particles and lyophilizing or freezing the aqueous composition, wherein the PVA is about 3K to about 125K, including for example about 13K or about 31 K. In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA to an aqueous composition comprising the particles and lyophilizing or freezing the aqueous composition, wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; and wherein the PVA is about 3K to about 125K, including for example about 13K or about 31 K. In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; and wherein at least about 50% (such as at least about 75%) of the PVA is hydrolyzed. In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA to an aqueous composition comprising the particles and lyophilizing or freezing the aqueous composition, wherein the PVA is about 3 to about 125K, including for example about 13K or about 31 K; and wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; wherein the PVA is about 3K to about 125K, including for example about 13K or about 31 K; and wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of preparing a lyophilized or frozen preparation of a composition comprising particles (such as particles having average diameter of no greater than about 200 nm) comprising a drug, wherein the particles comprise (such as coated with) PEG, wherein the particles comprise PLA or PLGA, the method comprising adding PVA to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%. In some embodiments, there is provided a method of preparing a lyophilized or frozen preparation of a composition comprising particles (such as particles having average diameter of no greater than about 200 nm) comprising a drug, wherein the particles comprise (such as coated with) PEG, wherein the particles comprise PLA or PLGA, the method comprising adding PVA to an aqueous composition comprising the particles and lyophilizing or freezing the aqueous composition, wherein the PVA is about 3K to about 125K, including for example about 13K or about 31 K. In some embodiments, there is provided a method of preparing a lyophilized or frozen preparation of a composition comprising particles (such as particles having average diameter of no greater than about 200 nm) comprising a drug, wherein the particles comprise (such as coated with) PEG, wherein the particles comprise PLA or PLGA, the method comprising adding PVA to an aqueous composition comprising the particles and lyophilizing or freezing the aqueous composition, wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of preparing a lyophilized or frozen preparation of a composition comprising particles (such as particles having average diameter of no greater than about 200 nm) comprising a drug, wherein the particles comprise (such as coated with) PEG, wherein the particles comprise PLA or PLGA, the method comprising adding PVA to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; and wherein the PVA is about 3K to about 125K, including for example about 13K or about 31 K. In some embodiments, there is provided a method of preparing a lyophilized or frozen preparation of a composition comprising particles (such as particles having average diameter of no greater than about 200 nm) comprising a drug, wherein the particles comprise (such as coated with) PEG, wherein the particles comprise PLA or PLGA, the method comprising adding PVA to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; and wherein at least about 50% (such as at least about 75%) of the PVA is hydrolyzed. In some embodiments, there is provided a method of preparing a lyophilized or frozen preparation of a composition comprising particles (such as particles having average diameter of no greater than about 200 nm) comprising a drug, wherein the particles comprise (such as coated with) PEG, wherein the particles comprise PLA or PLGA, the method comprising adding PVA to an aqueous composition comprising the particles and lyophilizing or freezing the aqueous composition, wherein the PVA is about 3K to about 125K, including for example about 13K or about 31 K; and wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of preparing a lyophilized or frozen preparation of a composition comprising particles (such as particles having average diameter of no greater than about 200 nm) comprising a drug, wherein the particles comprise (such as coated with) PEG, wherein the particles comprise PLA or PLGA, the method comprising adding PVA to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; wherein the PVA is about 3K to about 125K, including for example about 13K or about 31 K; and wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

Also provided are methods of preventing particle aggregation and/or particle size increase upon lyophilization and resuspension or freezing and thawing. For example, in some embodiments, there is provided a method of preventing particle aggregation and/or particle size increase upon lyophilization and resuspension or freezing and thawing of an aqueous composition comprising particles (such as particles having average diameter of no greater than about 200 nm) comprising a drug, wherein the particles comprise (such as coated with) PEG, the method comprising adding PVA to the aqueous particle composition prior to lyophilization or freezing. In some embodiments, there is provided a method of preventing particle aggregation and/or particle size increase upon lyophilization and resuspension or freezing and thawing of an aqueous composition comprising particles (such as particles having average diameter of no greater than about 200 nm) comprising a drug, wherein the particles comprise (such as coated with) PEG, the method comprising adding PVA to the aqueous particle composition prior to lyophilization or freezing, wherein the concentration of PVA in the aqueous particle composition is between about 0.05%

(w/v) to about 1% (w/v), including for example about 0.1% to about 0.3%. In some embodiments, there is provided a method of preventing particle aggregation and/or particle size increase upon lyophilization and resuspension or freezing and thawing of an aqueous composition comprising particles (such as particles having average diameter of no greater than about 200 nm) comprising a drug, wherein the particles comprise (such as coated with) PEG, the method comprising adding PVA to the aqueous particle composition prior to lyophilization or freezing, wherein the PVA is about 3K to about 125K, including for example about 13K or about 31 K. In some embodiments, there is provided a method of pie venting particle aggregation and/or particle size increase upon lyophilization and resuspension or freezing and thawing of an aqueous composition comprising particles (such as particles having average diameter of no greater than about 200 nm) comprising a drug, wherein the particles comprise (such as coated with) PEG, the method comprising adding PVA to the aqueous particle composition prior to lyophilization or freezing, wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of preventing particle aggregation and/or particle size increase upon lyophilization and resuspension or freezing and thawing of an aqueous composition comprising particles (such as particles having average diameter of no greater than about 200 nm) comprising a drug, wherein the particles comprise (such as coated with) PEG, the method comprising adding PVA to the aqueous particle composition prior to lyophilization or freezing, wherein the concentration of PVA in the aqueous particle composition is between about 0.05% (w/v) to about 1% (w/v), including for example about 0.1% to about 0.3%; and wherein the PVA is about 3K to about 125K, including for example about 13K or about 31 K. In some embodiments, there is provided a method of preventing particle aggregation and/or particle size increase upon lyophilization and resuspension or freezing and thawing of an aqueous composition comprising particles (such as particles having average diameter of no greater than about 200 nm) comprising a drug, wherein the particles comprise (such as coated with) PEG, the method comprising adding PVA to the aqueous particle composition prior to lyophilization or freezing, wherein the concentration of PVA in the aqueous particle composition is between about 0.05% (w/v) to about 1% (w/v), including for example about 0.1% to about 0.3%; and wherein at least about 50% (such as at least about 75%) of the PVA is hydrolyzed. In some embodiments, there is provided a method of preventing particle aggregation and/or particle size increase upon lyophilization and resuspension or freezing and thawing of an aqueous composition comprising particles (such as particles having average diameter of no greater than about 200 nm) comprising a drug, wherein the particles comprise (such as coated with) PEG, the method comprising adding PVA to the aqueous particle composition prior to lyophilization or freezing, wherein the PVA is about 3K to about 125K, including for example about 13K or about 31 K; and wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of preventing particle aggregation and/or particle size increase upon lyophilization and resuspension or freezing and thawing of an aqueous composition comprising particles (such as particles having average diameter of no greater than about 200 nm) comprising a drug, wherein the particles comprise (such as coated with) PEG, the method comprising adding PVA to the aqueous particle composition prior to lyophilization or freezing, wherein the concentration of PVA in the aqueous particle composition is between about 0.05% (w/v) to about 1% (w/v), including for example about 0.1% to about 0.3%; wherein the PVA is about 3K to about 125K, including for example about 13K or about 31 K; and wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, the method further comprises adding a sugar (such as sucrose) to the aqueous particle composition prior to lyophilization or freezing. Thus, for example, in some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA and a sugar (such as a sucrose, for example sucrose at a concentration of about 5% to about 20%) to an aqueous composition comprising the particles and lyophilizing or freezing the aqueous composition. In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA and a sugar (such as a sucrose, for example sucrose at a concentration of about 5% to about 20%) to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%. In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA and a sugar (such as a sucrose, for example sucrose at a concentration of about 5% to about 20%) to an aqueous composition comprising the particles and lyophilizing or freezing the aqueous composition, wherein the PVA is about 3K to about 125K, including for example about 13K or about 31 K. In some embodiments, there is provided a method of preparing a lyophilized or frozen preparation of a composition comprising particles (such as particles having average diameter of no greater than about 200 nm; comprising a drug, wherein the particles comprise (such as coated with) PEG, the method comprising adding PVA and a sugar (such as a sucrose, for example sucrose at a concentration of about 5% to about 20%) to an aqueous composition comprising the particles and lyophilizing or freezing the aqueous composition, wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA. In some embodiments, the sugar (such as sucrose) and the PVA are added simultaneously into the particle composition. In some embodiments, the sugar (such as sucrose) and the PVA are added sequentially into the particle composition.

In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA and a sugar (such as a sucrose, for example sucrose at a concentration of about 5% to about 20%) to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; and wherein the PVA is about 3K to about 125K, including for example, about 13K or about 31 K. In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA and a sugar (such as a sucrose, for example sucrose at a concentration of about 5% to about 20%) to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; and wherein at least about 50% (such as at least about 75%) of the PVA is hydrolyzed. In some embodiments, there is provided a method of preparing a lyophilized or frozen preparation of a composition comprising particles (such as particles having average diameter of no greater than about 200 nm) comprising a drug, wherein the particles comprise (such as coated with) PEG, the method comprising adding PVA and a sugar (such as a sucrose, for example sucrose at a concentration of about 5% to about 20%) to an aqueous composition comprising the particles and lyophilizing or freezing the aqueous composition, wherein the PVA is about 3K to about 125K, including for example about 13K or about 31 K; and wherein at least about 50% (such as at least about 75% )of the PVA is hydrolyzed. In some embodiments, the weight, ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles, lit some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA. In some embodiments, the sugar (such as sucrose) and the PVA are added simultaneously into the particle composition. In some embodiments, the sugar (such as sucrose) and the PVA are added sequentially into the particle composition.

In some embodiments, there is provided a method of preparing a lyophilized or frozen preparation of a composition comprising particles (such as particles having average diameter of no greater than about 200 nm) comprising a drug, wherein the particles comprise (such as coaled with) PEG, the method comprising adding PVA and a sugar (such as a sucrose, for example sucrose at a concentration of about 5% to about 20%) to an aqueous composition comprising the particles and lyophilizing or freezing the aqueous composition, wherein the concentration of PVA in the aqueous particle composition is between about 0.05% (w/v) to about 1% (w/v), including for example about 0.1% to about 0.3%; wherein the PVA is about 3K to about 125K, including for example about 13K or about 31 K; and wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments according to any one of the methods described above, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA. In some embodiments, the sugar (such as sucrose) and the PVA are added simultaneously into the particle composition. In some embodiments, the sugar (such as sucrose) and the PVA are added sequentially into the particle composition.

The PVA may be added to the aqueous composition immediately before lyophilization or freezing. For example, in some embodiments, PVA is admixed with the particles at least about any of 5 hours (hrs), 4 hrs, 3 hrs, 2 hrs, 1 hr, 0.75 hr, 0.5 hr, 0.25 hr before lyophilization or freezing. In some embodiments, PVA is admixed with the particles at any of about 5 hrs to about 4 hrs, about 4 hrs to about 3 hrs, about 3 hrs to about 2 hrs, about 2 hrs to about 1 hr, about 1 hr to about 0.75 hr, about 0.75 hr to about 0.5 hr, about 0.5 hr to about 0.25 hr before lyophilization or freezing. In some embodiments, PVA is admixed with the particles about any of 5 hrs, 4 hrs, 3 hrs, 2 hrs, 1 hr, 0.75 hr, 0.5 hr, 0.25 hr before lyophilization or freezing. In some embodiments. PVA is admixed with the particles no more than about 0.25 hr, 0.5 hr, 1 hr, 2 hrs, 3 hrs, 4 hrs, 5 hrs before lyophilization or freezing.

When used, the sugar (such as sucrose) can be added sequentially with the PVA or simultaneously with PVA. In some embodiments, sugar and PVA can be pre-mixed in a stock solution, and the stock solution mixture of sugar and PVA is admixed with the particle composition before lyophilization or freezing. In some embodiments, the sugar and PVA are added sequentially to the particle composition.

Solidification of the frozen particle composition during lyophilization can be accomplished, for example, by cooling below about the glass transition temperature of the formulation if the formulation is amorphous or below about the eutectic temperature if the formulation is crystalline. In some embodiments, the maximum temperature reached during the sublimation step is about the collapse temperature of the formulation. In some embodiments, removal of adsorbed water under vacuum continues until the water content of the composition by weight is at least about any of 1%, 0.5%, 0.1%, 0.05%, 0.01%. In some embodiments, removal of adsorbed water under vacuum continues till the water content of the composition by weight is any of about 1% to about 0.3%, about 0.5% to about 0.1%, about 0.1% to about 0.05%, about 0.05% to about 0.01%. In some embodiments, removal of adsorbed wafer under vacuum continues till the water content of the composition by weight is about any of 1%, 0.5%, 0.1%, 0.05%, 0.01%. In some embodiments, removal of adsorbed water under vacuum continues till the water content of the composition by weight is no more than about any of 0.01%, 0.05%, 0.1%, 0.5%, 1%.

The methods described herein can also be used for one or more of the following purposes: 1) reducing time of resuspending a lyophilized particle composition; 2) reducing time of thawing a frozen lyophilized particle composition; 3) preventing clogging of filters used in conjunction with the sterilization and/or administration of the particle composition; 4) reducing the in vivo toxicity of the particle composition; 5) increasing circulation time of administered particle composition; 6) increasing penetration of administered particle composition to the desired target site; and 7) improving therapeutic efficacy of the particle composition. The present application thus also encompasses any one or more of these aspects.

Thus, in some embodiments, there is provided a method of reducing time of resuspending a lyophilized particle composition comprising particles (such as particles having average diameter of no greater than about 200 nm) comprising a drug, wherein the particles comprise (such as coated with) PEG, the method comprising adding PVA to an aqueous composition comprising said particles prior to lyophilization. In some embodiments, there is provided a method of reducing time of resuspending a lyophilized particle composition comprising particles (such as particles having average diameter of no greater than about 200 nm) comprising a drug, wherein the particles comprise (such as coated with) PEG, the method comprising adding PVA to an aqueous composition comprising said particles prior to lyophilization, wherein the concentration of PVA in the aqueous particle composition is between about 0.05% (w/v) to about 1% (w/v), including for example about 0.1% to about 0.3%. In some embodiments, there is provided a method of reducing time of resuspending a lyophilized particle composition comprising particles (such as particles having average diameter of no greater than about 200 nm) comprising a drug, wherein the particles comprise (such as coated with) PEG, the method comprising adding PVA to an aqueous composition comprising said particles prior to lyophilization, wherein the PVA is about 3K to about 125K, including for example about 13K or about 31 K. In some embodiments, there is provided a method of reducing time of resuspending a lyophilized particle composition comprising particles (such as particles having average diameter of no greater than about 200 nm) comprising a drug, wherein the particles comprise (such as coated with) PEG, the method comprising adding PVA to an aqueous composition comprising said particles prior to lyophilization, wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of reducing time of thawing a frozen particle composition comprising particles (such as particles having average diameter of no greater than about 200 nm) comprising a drug, wherein the particles comprise (such as coated with) PEG, the method comprising adding PVA to an aqueous composition comprising said particles prior to freezing. In some embodiments, there is provided a method of reducing time of thawing a frozen particle composition comprising particles (such as particles having average diameter of no greater than about 200 nm) comprising a drug, wherein the particles comprise (such as coated with) PEG, the method comprising adding PVA to an aqueous composition comprising said particles prior to freezing, wherein the concentration of PVA in the aqueous particle composition is between about 0.05% (w/v) to about 1% (w/v), including for example about 0.1% to about 0.3%. In some embodiments, there is provided a method of reducing time of thawing a frozen particle composition comprising particles (such as particles having average diameter of no greater than about 200 nm) comprising a drug, wherein the particles comprise (such as coated with) PEG, the method comprising adding PVA to an aqueous composition comprising said particles prior to freezing, wherein the PVA is about 3K to about 125K, including for example about 13K or about 31 K. In some embodiments, there is provided a method of reducing time of thawing a frozen particle composition comprising particles (such as particles having average diameter of no greater than about 200 nm) comprising a drug, wherein the particles comprise (such as coated with) PEG, the method comprising adding PVA to an aqueous composition comprising said particles prior to freezing, wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25%

(w/v). In some embodiments, the PEG is covalently attached to the surface of the particles. In some embodiments, the PPG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of preventing clogging of filters used in conjunction with the sterilization and/or administration of a particle composition resuspended (or thawed) from a lyophized (or frozen) composition, said particle composition comprising particles (such as particles having average diameter of no greater than about 200 nm) comprising a drug, wherein the particles comprise (such as coated with) PEG, the method comprising adding PVA to an aqueous composition comprising said particles prior to lyophization (freezing). In some embodiments, there is provided a method of preventing clogging of filters used in conjunction with the sterilization and/or administration of a particle composition resuspended (or thawed) from a lyophized (or frozen) composition, said particle composition comprising particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the concentration of PVA in the aqueous particle composition is between about 0.05% (w/v) to about 1% (w/v), including for example about 0.1% to about 0.3%. In some embodiments, there is provided a method of preventing clogging of filters used in conjunction with the sterilization and/or administration of a particle composition resuspended (or thawed) from a lyophized (or frozen) composition, said particle composition comprising particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the PVA is about 3Ft to about 125K, including for example about 13K or about 31 K. In some embodiments, there is provided a method of preventing clogging of filters used in conjunction with the sterilization and/or administration of a particle composition resuspended (or thawed) from a lyophized (or frozen) composition, said particle composition comprising particles (such as particles having average diameter of no greater than about 200 nm) comprising a drug, wherein the particles comprise (such as coaled with) PEG, the method comprising adding PVA to an aqueous composition comprising said particles prior to lyophization (freezing), wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of reducing the in vivo toxicity of a particle composition resuspended (or thawed) from a lyophized (or frozen) composition, said particle composition comprising particles (such as particles having average diameter of no greater than about 200 nm) comprising a drug, wherein the particles comprise (such as coated with) PEG, the method comprising adding PVA to an aqueous composition comprising said particles prior to lyophization (freezing). In some embodiments, there is provided a method of reducing the in vivo toxicity of a particle composition resuspended (or thawed) from a lyophized (or frozen) composition, said particle composition comprising particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the concentration of PVA in the aqueous particle composition is between about 0.05% (w/v) to about 1% (w/v), including for example about 0.1% to about 0.3%. In some embodiments, there is provided a method of reducing the in vivo toxicity of a particle composition suspended (or thawed) from a lyophized (or frozen) composition, said particle composition comprising particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the PVA is about 3K to about 125K, including for example about 13K or about 31 K. In some embodiments, there is provided a method of preventing clogging of filters used in conjunction with the sterilization and/or administration of a particle composition resuspended (or thawed) from a lyophized (or frozen) composition, said particle composition comprising particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of increasing circulation time of an administered particle composition, wherein said particle composition is resuspended (or thawed) from a lyophized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing). In some embodiments, there is provided a method of increasing circulation time of an administered particle composition, wherein said particle composition is resuspended (or thawed) from a lyophized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the concentration of PVA in the aqueous particle composition is between about 0.05% (w/v) to about 1% (w/v), including for example about 0.1% to about 0.3%. In some embodiments, there is provided a method of increasing circulation time of an administered particle composition, wherein said particle composition is resuspended (or thawed) from a lyophized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the PVA is about 3K to about 125K, including for example about 13K or about 31 K. In some embodiments, there is provided a method of increasing circulation time of an administered particle composition, wherein said particle composition is resuspended (or thawed) from a lyophized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein at least about 30% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of increasing penetration of an administered particle composition to a desired target site, wherein said particle composition is resuspended (or thawed) from a lyophized (or frozen) composition and comprises particles (such as particles having average diameter of no greater than about 200 nm) comprising a drug, wherein the particles comprise (such as coated with )PEG, the method comprising adding PVA to an aqueous composition comprising said particles prior to lyophization (freezing). In some embodiments, there is provided a method of increasing penetration of an administered particle composition to a desired target site, wherein said particle composition is resuspended (or thawed) from a lyophized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the concentration of PVA in the aqueous particle composition is between about 0.05% (w/v) to about 1% (w/v), including for example about 0.1% to about 0.3%. In some embodiments, there is provided a method of increasing penetration of an administered particle composition to a desired target site, wherein said particle composition is resuspended (or thawed) from a lyophized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the PVA is about 3K to about 125K, including for example about 13K or about 31 K. In some embodiments, there is provided a method of increasing penetration of an administered particle composition to a desired target site, wherein said particle composition is resuspended (or thawed) from a lyophized (or frozen) composition and comprises particles (such as particles having average diameter of no greater than about 200 nm) comprising a drug, wherein the particles comprise (such as coated with) PEG, the method comprising, adding PVA to an aqueous composition comprising said particles prior to lyophization (freezing), wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

In some embodiments, there is provided a method of improving therapeutic efficacy of a particle composition, wherein said particle composition is a lyophilized (or frozen) composition or resuspended (or thawed) from a lyophilized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing). In some embodiments, there is provided a method of improving therapeutic efficacy of a particle, composition, wherein said particle composition is a lyophilized (or frozen) composition or resuspended (or thawed) from a lyophilized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the concentration of PVA in the aqueous particle composition is between about 0.05% (w/v) to about 1% (w/v), including for example about 0.1% to about 0.3%. In some embodiments, there is provided a method of improving therapeutic efficacy of a particle composition, wherein said particle composition is a lyophilized (or frozen) composition or resuspended (or thawed) from a lyophilized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein the PVA is about 3K to about 125K, including for example about 13K or about 31 K. In some embodiments, there is provided a method of improving therapeutic efficacy of a particle composition, wherein said particle composition is a lyophilized (or frozen) composition or resuspended (or thawed) from a lyophilized (or frozen) composition and comprises particles (such as particles having average diameter of no greater than about 200 nm) comprising a drug, wherein the particles comprise (such as coated with) PEG, the method comprising adding PVA to an aqueous composition comprising said particles prior to lyophization (freezing), wherein at least about 50% (such as at least about 75%) of the PVA is hydrolyzed. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is a structural component of the particles. In some embodiments, the aqueous particle composition to which the PVA is added is substantially free (such as free) of PVA prior to the addition of PVA.

Pharmaceutical Compositions

Also provided are pharmaceutical compositions produced by the methods described herein. For example, in some embodiments, there is provided a pharmaceutical composition comprising particles (such as particles having average diameter of no greater than about 200 nm) comprising a drug, wherein the particles comprise (such as coated with) PEG, wherein the composition is produced by a method comprising adding PVA to an aqueous composition comprising the particles and lyophilizing or freezing the aqueous composition. In some embodiments, the PEG is covalently attached to the surface of the particles. In some embodiments, the PEG is tethered to the surface of the particles by hydrophobic or charge interactions. In some embodiments, the PEG is one of the structural components of the particles. In some embodiments, the particles comprise PLA or PLGA. In some embodiments, the composition further comprises a sugar (for example a sucrose, such as sucrose at a concentration of between about 5% to about 20%). In some embodiments, the molecular weight of the PEG is at least about any of 2 kDa, 3 kDa, 5 kDa, 6 kDa, or 8 kDa. In some embodiments, the weight ratio of PEG to the particles is at least about 20%, 30%, 40%, 50%, 60%, or 70%.

In some embodiments, there is provided a pharmaceutical composition comprising particles comprising a drug, wherein the particles comprise (such as coated with) PEG, wherein the composition further comprises PVA, and wherein less than about 2% of the total PVA in the pharmaceutical composition is associated with the particles. In some embodiments, the composition is lyophilized or frozen. In some embodiments, the composition is an aqueous suspension resuspended from a lyophilized or frozen composition. In some embodiments, the composition is an aqueous suspension. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is one of the structural components of the particles. In some embodiments, the particles comprise PLA or PLGA. In some embodiments, the composition further comprises a sugar (for example a sucrose, such as sucrose at a concentration of between about 5% to about 20%). In some embodiments, the molecular weight of the PEG is at least about any of 2 kDa, 3 kDa, 5 kDa, 6 kDa, or 8 kDa. In some embodiments, the weight ratio of PEG to the particles is at least about 20%, 30%, 40%, 50%, 60%, or 70%.

In some embodiments, there is provided a pharmaceutical composition comprising particles (such as particles having average particle size of no greater than about 200 nm) comprising a drug, wherein the particles comprise (such as coated with) PEG, wherein the composition further comprises PVA, and wherein less than about 2% of the total PVA in the pharmaceutical composition is associated with the particles, wherein the concentration of PVA in the particle composition is between about 0.05% to about 1%, including for example between about 0.1%, to about 0.3%. In some embodiments, there is provided a pharmaceutical composition comprising particles (such as particles having average particle size of no greater than about 200 nm) comprising a drug, wherein the particles comprise (such as coated with) PEG, wherein the composition further comprises PVA, and wherein less than about 2% of the total PVA in the pharmaceutical composition is associated with the particles, wherein the PVA is about 3K to about 125K, including for example about 13K or about 31 K. In some embodiments, there is provided a pharmaceutical composition comprising particles (such as particles having average particle size of no greater than about 200 nm) comprising a drug, wherein the particles comprise (such as coated with) PEG, wherein the composition further comprises PVA, and wherein less than about 2% of the total PVA in the pharmaceutical composition is associated with the particles, wherein the PVA is at least, about 50% hydrolyzed, including for example at least about 75% hydrolyzed. In some embodiments, the composition is an aqueous suspension. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is one of the structural components of the particles. In some embodiments, the particles comprise PLA or PLGA. In some embodiments, the composition further comprises a sugar (for example a sucrose, such as sucrose at a concentration of between about 5% to about 20%). In some embodiments, the molecular weight of the PEG is at least about any of 2 kDa, 3 kDa, 5 kDa, 6 kDa, or 8 kDa. In some embodiments, the weight ratio of PEG to the particles is at least about 20%, 30%, 40%, 50%, 60%, or 70%.

In some embodiments, there is provided a pharmaceutical composition comprising particles (such as particles having average particle size of no greater than about 200 nm) comprising a drug, wherein the particles comprise (such as coated with) PEG, wherein the composition further comprises PVA, and wherein less than about 2% of the total PVA in the pharmaceutical composition is associated with the particles, wherein the concentration of PVA in the particle composition is between about 0.05% to about 1%, including for example between about 0.1% to about 0.3%; wherein the PVA is about 3K to about 125K, including for example about 13K or about 31 K. In some embodiments, there is provided a pharmaceutical composition comprising particles (such as particles having average particle size of no greater than about 200 nm) comprising a drug, wherein the particles comprise (such as coated with) PEG, wherein the composition further comprises PVA, and wherein less than about 2% of the total PVA in the pharmaceutical composition is associated with the particles, wherein the PVA is at least about 50% hydrolyzed, including for example at least about 75% hydrolyzed. In some embodiments, the composition is an aqueous suspension. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is one of the structural components of the particles. In some embodiments, the particles comprise PLA or PLGA. In some embodiments, the composition further comprises a sugar (for example a sucrose, such as sucrose at a concentration of between about 5% to about 20%). In some embodiments, the molecular weight of the PEG is at least about any of 2 kDa, 3 kDa, 5 kDa, 6 kDa, or 8 kDa. In some embodiments, the weight ratio of PEG to the particles is at least about 20%, 30%, 40%, 50%, 60%, or 70%.

In some embodiments, there is provided a pharmaceutical composition comprising particles (such as particles having average particle size of no greater than about 200 nm) comprising a drug, wherein the particles comprise (such as coated with) PEG, wherein the composition further comprises PVA, and wherein less than about 2% of the total PVA in the pharmaceutical composition is associated with the particles, wherein the concentration of PVA in the particle composition is between about 0.05% to about 1%, including for example between about 0.1% to about 0.3%: wherein the PVA is at least about 50% hydrolyzed, including for example at least about 75% hydrolyzed. In some embodiments, the composition is an aqueous suspension. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is one of the structural components of the particles. In some embodiments, the particles comprise FLA or PLGA. In some embodiments, the composition further comprises a sugar (for example a sucrose, such as sucrose at a concentration of between about 5% to about 20%). In some embodiments, the molecular weight of the PEG is at least about any of 2 kDa, 3 kDa, 5 kDa, 6 kDa, or 8 kDa. In some embodiments, the weight ratio of PEG to the particles is at least about 20%, 30%, 40%, 50%, 60%, or 70%.

In some embodiments, there is provided a pharmaceutical composition comprising particles (such as particles having average particle size of no greater than about 200 nm) comprising a drug, wherein the particles comprise (such as coated with) PEG, wherein the composition further comprises PVA, and wherein less than about 2% of the total PVA in the pharmaceutical composition is associated with the particles, wherein the PVA is about 3 K to about 125K, including for example about 13K or about 31 K; and wherein the PVA is at least about 50% hydrolyzed, including for example at least about 75% hydrolyzed. In some embodiments, the composition is an aqueous suspension. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is one of the structural components of the particles. In some embodiments, the particles comprise PLA or PLGA. In some embodiments, the composition further comprises a sugar (for example a sucrose, such as sucrose at a concentration of between about 5% to about 20%). In some embodiments, the molecular weight of the PEG is at least about any of 2 kDa, 3 kDa, 5 kDa, 6 kDa, or 8 kDa. In some embodiments, the weight ratio of PEG to the particles is at least about 20%, 30%, 40%, 50%, 60%, or 70%.

In some embodiments, there is provided a pharmaceutical composition comprising particles (such as particles having average particle size of no greater than about 200 nm) comprising a drug, wherein the particles comprise (such as coated with) PEG. wherein the composition further comprises PVA, and wherein less than about 2% of the total PVA in the pharmaceutical composition is associated with the particles, wherein the concentration of PVA in the particle composition is between about 0.05% to about 1%, including for example between about 0.1% to about 0.3%; wherein the PVA is about 3K to about 125K, including for example about 13K or about 31 K; and wherein the PVA is at least about 50% hydrolyzed, including for example at least about 75% hydrolyzed. In some embodiments, the composition is an aqueous suspension. In some embodiments, the weight ratio of the PVA to the particles in the resultant composition is less than about 0.2:1. In some embodiments, the concentration of the particles in the aqueous particle composition is about 1% to about 25% (w/v). In some embodiments, the PEG is covalently attached to the surface of the particles. In some embodiments, the PEG is tethered to the surface of the particles by hydrophobic or charge interactions. In some embodiments, the PEG is one of the structural components of the particles. In some embodiments, the molecular weight of the PEG is at least about any of 2 kDa, 3 kDa, 5 kDa, 6 kDa, or 8 kDa. In some embodiments, the weight ratio of PEG to the particles is at least about 20%, 30%, 40%, 50%, 60%, or 70%.

In some embodiments according to any one of the pharmaceutical compositions described above, the weight ratio of the PVA to the particles in the composition is less than about 0.2:1. In some embodiments according to any one of the pharmaceutical compositions described above, the concentration of the particles in the aqueous particle composition is about 1% to about 25% (w/v). In some embodiments, the particles comprise PL A or PLGA. In some embodiments, the composition further comprises a sugar (for example a sucrose, such as sucrose at a concentration of between about 5% to about 20%).

In some embodiments, the pharmaceutical composition is contained in vial, such as a sealed vial.

The amount of PVA associated with the particles can be determined by carrying out methods known in the art (see, e.g., Wendorf et al., *J. Pharma. Sci.*, 95, 12, (2006)). For example, the particles can be separated from the rest of the composition by suspending them in a suitable solvent phase, centrifuging the suspension and separating the supernatant. The PVA containing particles and the supernatant are hydrolyzed in 2N NaOH and reacted with boric acid in the presence of iodine solution. The reaction of PVA with iodine and boric acid results in a greenish complex whose absorption is measured and concentration of PVA calculated.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6, 5, 7, or 8 (such as about 8). The composition can also be made to be isotonic with blood by the addition of a suitable tonicity modifier, such as glycerol.

As used herein, an aqueous composition is a composition that includes, for example, a medium that is 50% or more water, by weight, based on the weight of the medium. Some aqueous compositions are 75% or more, or 90% or more, water by weight, based on the weight of the medium. Ingredients other than water may be dissolved in the aqueous medium, dispersed in the aqueous medium, or any combination thereof.

The compositions described herein can include other agents, excipients, or stabilizers to improve properties of the composition. For example, to increase stability by increasing the negative zeta potential of particles, certain negatively charged components may be added. Such negatively charged components include, but are not limited to bile salts, bile acids, glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidyl-choline, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearoylphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

PVA

As described herein, PVA refers to polyvinyl alcohol, including partially hydrolyzed polyvinyl alcohol and mixtures containing the same. The term PVA used herein also includes PVA contained within a co-polymer, such as PVA-PVP polymer or PVA-PEG polymer, so long as the PVA component in the co-polymer is more than about 50% (w/w). In some embodiments the PVA can include co-polymers of PVA with methylmethacrylate and/or alkenes. The amount of the co-polymer is added controlled such that a desired ratio of PVA in the composition can be obtained.

The concentration by weight of the PVA in the aqueous particle composition in some embodiments is at least about any of 0.05%, 0.1%, 0.2%, 0.5%, 0.4%, 0.5%, 0.6%, 0.7%, 0.8%, 0.9%, 1%. In some embodiments, the concentration by weight of the PVA in the aqueous particle composition is any of about 0.05 to about 0.1%, about 0.1% to about 0.2%, about 0.2% to about 0.3%, about 0.3% to about 0.4%, about 0.4% to about 0.5%, about 0.5% to about 0.6%, about 0.6% to about 0.7%, about 0.7% to about 0.8%, about 0.8% to about 0.9%, about 0.9% to about 1.0%. In some embodiments, the concentration by weight of the PVA in the aqueous particle composition is about any of 0.05%, 0.1%, 0.2%, 0.3%, 0.4%, 0.5%, 0.6%, 0.7%, 0.8%, 0.9%, 1%. In some embodiments, the concentration by weight of the PVA in the aqueous particle composition is at most about any of 1.0%, 0.9%, 0.8%, 0.7%, 0.6%, 0.5%, 0.4%, 0.3%, 0.2%, 0.1%, 0.05%.

The molecular weight of PVA in some embodiments can be at least about any of 1 KDa, 5 KDa, 7 KDa, 10 KDa, 11 KDa, 12 KDa, 13KDa, 15 KDa, 20 KDa, 25 KDa, 31 KDa, 40 KDa, 60 KDa, 85 KDa, 75 KDa, 90 KDa, 100 KDa, 115 KDa, 120 KDa, 122 KDa, 123 KDa, 124 KDa, 125 KDa, 126 KDa, 127 KDa, 130 KDa, 140 KDa, 150 KDa. In some embodiments, the molecular weight of PVA is any of about 1 KDa to about 25 KDa, about 25 KDa to about 50 KDa, about 50 KDa to about 75 KDa, about 75 KDa to about 100 KDa, about 100 KDa to about 125 KDa, about 125 KDa to about 150 KDa. In some embodiments. the molecular weight of PVA is about any of 1 KDa, 5 KDa, 7 KDa, 10 KDa, 11 KDa, 12 KDa, 13 KDa, 15 KDa, 20 KDa, 23 KDa, 31 KDa, 40 KDa, 60 KDa, 83 KDa, 75 KDa, 90 KDa, 100 KDa, 115 KDa, 120 KDa, 122 KDa, 123 KDa, 124 KDa, 123 KDa, 126 KDa, 127 KDa, 130 KDa, 140 KDa, 150 KDa. In some embodiments, the molecular weight of PVA is no more than about any of 150 KDa, 140 KDa, 130 KDa, 127 KDa, 126 KDa, 125 KDa, 124 KDa, 123 KDa, 122 KDa, 120 KDa, 115 KDa, 100 KDa, 90 KDa, 75 KDa, 85 KDa, 60 KDa, 40 KDa, 31 KDa, 25 KDa, 20 KDa, 15 KDa, 13 KDa, 12 KDa, U KDa, 10 KDa, 7 KDa, 5 KDa, 1 KDa.

In some embodiments, the PVA is hydrolyzed. For example, in some embodiments, the PVA is at least about 50% hydrolyzed. In some embodiments, the percentage of PVA hydrolyzed by weight is at least about any of 1.0%, 10%, 20%, 30%, 40%, 50%, 60%, 70%, 80%, 90%, or 99%. In some embodiments, the percentage of hydrolyzed PVA by weight is any of about 1.0% to about 10%, about 10% to about 20%, about 20% to about 30%, about 30%, to about 40%, about 40%, to about 50%, about 50%, to about 60%, about 60% to about 70%, about 70% to about 80%, about 80% to about 90%, about 90% to about 99%. In some embodiments, the percentage of hydrolyzed PVA by weight is about any of 1.0%, 10%, 20%, 30%, 40%, 50%, 60%, 70%, 80%, 90%, 99%. In some embodiments, the percentage of hydrolyzed PVA by weight is at most about any of 99%, 90%, 80%, 70%, 60%, 50%, 40%, 30%, 20%, 10%, 1.0%.

The weight ratio of the PVA to the particles in the composition in some embodiments is less than about 0.2:1, including for example any of about 0.01:1 to about 0.05:1, about 0.05:1 to about 0.1:1, about 0.1:1 to about 0.15:1, about 0.15:1 to about 0.2:1. In some embodiments, the weight ratio of the PVA to the particles in the composition is no greater than about any of 0.01:1, 0.05:1, 0.1:1, 0.15:1, 0.2:1. In some embodiments, the weight ratio of the PVA to the particles in the resultant composition is no less than about any of 0.2:1, 0.15:1, 0.1:1, 0.05:1, 0.01:1.

In some embodiments, when the composition is an aqueous composition the concentration by weight of the PVA in the composition is between about 0.05% to about 1%, the molecular weight of PVA is about 1 KDa to about 150 KDa, and the percentage by weight of PVA hydrolyzed is between about 1% to about 99%.

In some embodiments, when the composition is an aqueous composition the concentration by weight of the PVA is between about 0.1% to about 0.3%, the molecular weight of PVA is about 1 KDa to about 150 KDa, and the percentage by weight of PVA hydrolyzed is between about 1% to about 99%.

In some embodiments, when the composition is an aqueous composition the concentration by weight of the PVA is between about 0.1% to about 0.3%, the molecular weight of PVA is about 13 KDa to about 31 KDa, and the percentage by weight of PVA hydrolyzed is between about 1% to about 99%.

In some embodiments, when the composition is an aqueous composition the concentration by weight of the PVA is between about 0.1% to about 0.3% the molecular weight of PVA is about 13 KDa to about 31 KDa, and the percentage by weight of PVA hydrolyzed is between about 75% to about 85%.

PEG-Containing Particles

Although the term "particles" is primarily used to refer to solid particles, it is to be understood that the methods described herein are also applicable to liposomes, micelles, and the like, so long as they comprise PPG (e.g., are coated with PEG) as herein described. The methods and compositions described in the present application thus also encompass liposomes and micelles.

In some embodiments, the particles have an average particle size of no greater than about 1 micron. In some embodiments, the particles have an average particle size of no greater than about any of 900 nm, 800 nm, 700 nm, 600 nm, 500 nm, 400 nm, 300 nm. In some embodiments, the particles have an average particle size of no greater than about 200 nm. In some embodiments, the particle have an average particle size of no greater than about 150 nm, 100 nm, 90 nm, or 80 nm. Average particle size can be determined by any methods known in the art. For example, in some embodiments, the average particle size refers to the Z-average of a population of particles determined by routine method such as dynamic light scattering.

In some embodiments, the particles have a particle size of no greater than about 1 micron. In some embodiments, the particles have a particle size of no greater than about any of 900 nm, 800 nm, 700 nm, 600 nm, 500 nm, 400 nm, 300 nm. In some embodiments, the particles have a particle size of no greater than about 200 nm. In some embodiments, the particle have a particle size of no greater than about 150 nm, 100 nm, 90 nm, or 80 nm.

The particles described herein in some embodiments have an average size of no greater than about 200 nm. In some embodiments, the average size of the particles in the particle composition is at least about any of 1000 nm, 900 nm, 800 nm, 700 nm, 600 nm, 500 nm, 400 nm, 300 nm, 200 nm, 100 nm, 50 nm. In some embodiments, the average size of the particles in the particle composition is any of about 1000 nm to about 900 nm, about 900 nm to about 800 nm, about 800 nm to about 700 nm, about 700 nm to about 600 nm, about 600 nm to about 500 nm, about 500 nm to about 400 nm, about 400 nm to about 300 nm, about 300 nm to about 200 nm, about 200 nm to about 100 nm, about 100 nm to about 50 nm. In some embodiments, the average size of the particles in the particle composition is no more than about any of 50 nm, 100 nm, 200 nm, 300 nm, 400 nm, 500 nm, 600 nm, 700 nm, 800 nm, 900 nm, 1000 nm. In some embodiments, the average size of the particles does not change more than any of about 0%, 1%, 2%, 3%, 4%, 5%, 6%, 7%, 8%, 9%, 10% upon lyophilization and suspension or freezing and thawing. In some embodiments, the average size of the particles changes any of about 0% to about 1%, about 1% to about 2%, about 2% to about 3%, about 3% to about 4%, about 4% to about 5%, about 5% to about 6%, about 6% to about 7%, about 7% to about 8%, about 8% to about 9%, about 9% to about 10%, about 10% to about 11%, about 11% to about 12%, about 12%, to about 13%, about 13% to about 14%, or about 14% to about 15% upon lyophilization and resuspension or freezing and thawing.

The concentration (w/v) of the particles in aqueous composition in some embodiments can be at least about any of 1%, 5%, 10%, 15%, 20%, 25%. In some embodiments, the concentration of the particles in the aqueous composition is any of about 1% to about 5%, about 5% to about 10%, about 10% to about 15%, about 15% to about 20%, about 20% to about 25%. In some embodiments, the concentration of the particles in aqueous composition is about any of 1%, 5%, 10%, 15%, 20%, 25%. In some embodiments, the concentration of the particles in aqueous composition is at most about any of 25%, 20%, 15%, 10%, 5%, 1%.

The particles described herein comprise PEG. The term "PEG" as used herein means any of several condensation polymers of ethylene glycol. PEG is also known as polyoxyethylene, polyethylene oxide, polyglycol, and polyether glycol. The end groups of PEG can be derivatized to in a variety of ways to include non-reactive groups or reactives, for example for attaching a targeting moiety (such as antibody or antibody fragments). In some embodiments, for example, PEG can be any hydrophilic polymer soluble in water containing ether groups linked by 2 or 3 carbon atoms. In some embodiments, PEG can include branched polyethylene glycol, non-branched polyethylene glycol and a mixture of branched and non branched polyethylene glycols. In some embodiments PEG may include polypropylene glycols, and also block or random copolymers including the two types of units. The term also includes derivatives of the terminal hydroxyl groups, which can be modified (1 or both ends) so as to introduce alkoxy, acrylate, methacrylate, alkyl, amino, phosphate, isothiocyanate, sulfhydryl, mercapto and/or sulfate groups. In some embodiments PEG can have substituents in the alkylene groups. In some embodiments of the invention the polyethylene glycol does not have substituted hydroxyl groups or alkylene groups.

In some embodiments, the particles are coated with PEG. In some embodiments, the PEG is covalently attached to the surface of the particle. Alternatively, in some embodiments the PEG is tethered to the surface of particles by hydrophobic or charge interactions. In some embodiments, the PEG is one of the structural components of the particles. For example, the PEG can be part of a co-polymer that forms the core of structural component of the particles.

In some embodiments, the molecular weight of PEG is at least about any of 400 Da, 1 KDa, 5 KDa, 10 KDa, 15 KDa, 20 KDa, 25 KDa, 30 KDa, 35 KDa. In some embodiments, the molecular weight of PEG is any of about 400 Da to about 1 KDa, about 1 KDa to about 5 KDa, about 5 KDa to about 10 KDa, about 10 KDa to about 15 KDa, about 15 KDa to about 20 KDa, about 20 KDa to about 25 KDa, about 25 KDa to about 30 KDa, about 30 KDa to about 35 KDa. In some embodiments, the molecular weight of PEG is about any of 400 Da, 1 KDa, 5 KDa, 10 KDa, 15 KDa, 20 KDa, 25 KDa, 30 KDa, 35 KDa. In some embodiments, the molecular weight of PEG is no more than about any of 35 KDa, 30 KDa, 25 KDa, 20 KDa, 15 KDa, 10 KDa, 5 KDa, 1 KDa, 400 Da.

In some embodiments, the weight ratio of PEG to the particles is at least about 20%, 30%, 40%, 50%, 60%, or 70%.

In some embodiments, the following polyethylene glycol derivatives can be used:

Polyoxyethylene esters: PEG monomethyl ether monosuccinimidyl succinate ester; PEG monomethylether monocarboxymethyl ether; PEG adipate; PEG distearate; PEG monostearate; PEG hydroxystearate; PEG dilaurate; PEG dioleate, PEG monooleate, PEG monoricinoleate; PEG coconut oil esters.

Polyoxyethylene alkyl ethers: PEG monomethylether or methoxy PEG (mPEG); PEG dimethyl ether.

Others: Poly(ethylene glycol terephthalate); polyoxyethylene derivatives and sorbitan esters and fatty acids; ethylene oxide and propylene oxide copolymers; ethylene oxide with acrylamide copolymers.

PEG derivatives: O,O'-Bis-(2-aminoethyl)polyethyleneglycol (DAE-PEG 2000); O,O'-Bis-(2-aminopropyl)polypropylene glycol-polyethylene glycol-polypropylene glycol.

In some embodiments of the invention the polyethylene glycol used has terminal functional groups different from the hydroxyl group, such as amino groups, phenol, aldehyde, isothiocyanate, —SH groups, etc. These groups for example, can in turn be substituted and have functional groups. Therefore, in one embodiment the polyethylene glycol used in manufacturing PEG-coated particles is O,O'-bis-(2-aminoethyl) polyethylene glycol 2000 (DAE-PEG 2000). In this case it is thought that the structure of the PEG-coated particle is not the "brush" type structure because the chains would be joined at the two ends, giving rise to a "loop" type shape. The polyethylene glycol derivatives can be branched, un-branched or a mixture thereof.

The chemical structures of some of polyalkylene glycols corresponding to the previously mentioned groups with different types of functional groups are illustratively provided below:
a) $H(OCH_2CH_2)nOH$
b) $H_3C(OCH_2CH_2)nOH$
c) $H_2N(CH_2CH_2O)nCH_2CH_2NH_2$
d) $H_2NCHCH_3CH_2(OCHCH_3CH_2)(OCH_2CH_2)n(OCH_2CHCH_3)NH_2$ Specific examples include, but are not limited to:
a) polyethylene glycol 400, 1000 or 2000 (PEG 400, PEG 1000 or PEG 2000);
b) polyethylene glycol methyl ether 2000 (mPEG 2000);
c) O,O'-Bis-(2-aminoethyl)polyethylene glycol 2000 (DAE-PEG 2000);
d) O,O'-Bis-(2-aminopropyl)polypropylene glycolpolyethylene glycolpolypropylene glycol (DAP-PEG 2000);

In some embodiments, the particle has a solid core containing a drug and poly (alkylene glycol) moieties on the surface. In some embodiments, the terminal hydroxyl group of the poly(alkylene glycol) can be used to covalently attach biologically active molecules, or molecules affecting the charge, lipophilicity or hydrophilicity of the particle, onto the surface of the particle.

In some embodiments, a particle is provided that includes a drug and a diblock, triblock, or multiblock copolymer of poly(alkylene glycol) with poly(lactic co-glycolic acid) or poly-lactic acid. In another embodiment, a particle is provided that includes a drug and a copolymer of poly(alkylene glycol) with a polyanhydride, polyhydroxy butyric acid, polyorthoesters other than the homopolymer of lactic acid, polysiloxanes, polycaprolactone. or copolymers prepared from the monomers of these polymers, wherein the copolymer can be of diblock, triblock, or multiblock structure. Alternatively, the particle can include a drug and a copolymer of the form poly(alkylene glycol)-[poly(lactic co-glycolic acid) or poly(lactic acid)]-poly(alkylene glycol). In yet another embodiment, the particle includes a drug and a copolymer of a poly (lactic acid) or poly(glycolic acid), with two or more moieties of poly(alkylene glycol). Alternatively, the particle can include a drug and a copolymer of a poly(lactic co-glycolic acid), poly(lactic acid), or poly (glycolic acid) with poly(alkylene glycol), wherein the copolymer is blended with poly(lactic-co-glycolic acid). In another embodiment the poly(alkylene glycol) can be bound to a compound that affects the charge or lipophilicity or hydrophilicity of the particle.

In some embodiments, the particle is biodegradable. In some embodiments the particles are biocompatible. In some embodiments the invention relates to particles containing PEG formed from a biodegradable polymer. Biodegradable polymers known in the state of the art which give rise to the formation of particles can be used. These polymers include, among others, polyhydroxyacids such as polylactic and polyglycolic acid and copolymers thereof (for example PLGA), polyanhydrides, polyesters and polysaccharides, for example chitosan. The term "biodegradable" in this description refers to polymers which dissolve or degrade in a period of time which is acceptable for the desired application, in this case in vivo therapy, once they are exposed to a physiological solution of pH 6-9 and a temperature comprised between 25° C. and 40° C.

Methods of making PEG-containing particles of drugs are known in the art. See, e.g., Vauthier et al., Pharmaceutical Research, "Methods for the preparation and manufacture of polymeric particles," Vol. 26, No. 5, 2009; De Jaeghere et al., Pharmaceutical Research, "Formulation and lyophilization of poly(lactic acid-co-ethylene oxide) particles: influence on physical stability and in vitro cell uptake", Vol. 16, No. 6, 1999. By way of example, the drug is admixed with PEG-containing polymers such as PEG-PLGA, in a water/oil emulsion. This mixture is then subjected to homogenization, for example by using a high pressure homogenizer. The organic solvent can then be removed by evaporation, spray drying, or dilution.

To carry out the methods described herein, PVA can be added to the aqueous composition before lyophilization or freezing. In some embodiments, sugar and PVA can be admixed with the particle composition before lyophilization or freezing.

The methods of making PEG-containing particles can further comprise a step of sterilization. Sterilization methods such as sterile filtration and gamma-irradiation are known in the art. PVA can be added either before or after the sterilization step. In some embodiments, one or more steps described in the methods of making PEG-containing particles are carried out under aseptic conditions. PVA can be added before, during, or after the aspectic process.

Drugs

Drugs described herein include water soluble drugs and poorly water soluble drugs which can be, for example, drugs with solubility in water less than about 10 mg/ml at about 20-25° C., including for example drugs with solubility less than about any of 5, 2, 1, 0.5, 0.2, 0.1, 0,05, 0.02, or 0.01 mg/ml. Drugs described herein can be, for example, anticancer or antineoplastic agents, antimicrotubule agents, immunosuppressive agents, anesthetics, hormones, agents for use in cardiovascular disorders, antiarrhythmics, antibiotics, antifungals, antihypertensives, antiasthmatics, anti-inflammatory agents, antiarthritic agents, vasoactive agents, analgesics/antipyretics, antidepressants, antidiabetics, antifungal agents, anti-inflammatories, antianxiety agents, immunosuppressive agents, antimigraine agents, sedatives, antianginal agents, antipsychotic agents, antimanic agents, antiarthritic agents, antigout agents, anticoagulants, thrombolytic agents, antifibrinolytic agents, hemorheologic agents, anti platelet agents, anticonvulsants, antiparkinson agents, antihistamines/antipruritics, agents useful for calcium regulation, antiviral agents, antimicrobials, anti-infectives. bronchodialators, hormones, hypoglycemic agents, hypolipidemic agents, antiulcer/antirefluxagents, antinauseants/antiemetics, and oil-25 soluble vitamins (e.g., vitamins A, D, E, K, and the like). In some embodiments, the drug is any one of a protein, DNA, RNA (including siRNA), and the like.

In some embodiments, the drug is an antineoplastic agent. In some embodiments, the drug is a chemotherapeutic agent. Suitable drugs include, but are not limited to, taxanes (such as paclitaxel, docetaxel, ortataxel and other taxanes), romidepsin, epothilones, camptothecins, colchicines, geladanamycins, amiodarones, thyroid hormones, amphotericin, corticosteroids, propofol, melatonin, cyclosporine, rapamycin (sirolimus) and derivatives, tacrolimus, mycophenolic acids, ifosfamide, vinorelbine, vancomycin, gemcitabine, SU5416, thiotepa, bleomycin, diagnostic radiocontrast agents, and derivatives thereof. Other poorly water soluble pharmaceutical agents that are useful in the inventive compositions are described in, for example, U.S. Pat. Nos. 5,916,596, 6,096,331, 6,749,868, and 6,537,539. Additional examples of drugs include those compounds which are poorly water soluble and which are listed in the "Therapeutic Category and Biological Activity Index" of The Merck Index (12 th Edition, 1996).

In some embodiments, the drug is any of (and in some embodiments selected from the group consisting of) paclitaxel, docetaxel, ortataxel or other taxane or taxane analog, 17-allyl amino geldanamycin (17-AAG), 18-derivatized geldanamycin, camptothecin, propofol, amiodarone, cyclosporine, epothilone, radicicol, combretastatin, rapamycin, amphotericin, liothyronine, epothilone, colchicine, thiocolchicine and its dimers, thyroid hormone, vasoactive intestinal peptide, corticosteroids, melatonin, tacrolimus, mycophenolic acids, epothilones, radicicols, combretastatins, and analog or derivative thereof. In some embodiments, the drug is any of (and in some embodiments selected from the group consisting of) paclitaxel, docetaxel, ortataxel or other taxanes, geldanamycin, 17-allyl amino geldonamycin, thiocolchicine and its dimers, rapamycin, cyclosporine, epothilone, radicicol, and combretastatin. In some embodiments, the drug is rapamycin. In some embodiments, the drug is 17-AAG. In some embodiments, the drug is a thiocolchicine dimer (such as IDN5404).

In some embodiments, the drug is a taxane or derivative thereof, which includes, but is not limited to, paclitaxel, docetaxel and IDN5109 (ortataxel), or a derivative thereof. In some embodiments the composition comprises a noncrystalline and/or amorphous taxane (such as paclitaxel or a derivative thereof). In some embodiments, the composition is prepared by using an anhydrous taxane (such as anhydrous docetaxel or a derivative thereof). Anhydrous docetaxel has been shown to produce a more stable formulation than can be made with a hydrated docetaxel such as docetaxel trihydrate or hemi-hydrate.

Sugar

In some embodiments, sugar is added to the particle composition. Exemplary sugars include, for example, sucrose, maltose, trehalose, xylitol, glucose, fructose, lactose, mannitol, and dextrin.

In some embodiments, the concentration of sugar (such as sucrose) by weight, in the aqueous composition, is at least about any of 1%, 5%, 10%, 15%, 20% (w/v). In some embodiments, the concentration of sugar (such as sucrose) by weight, in the aqueous composition, is any of about 1% to about 5%, about 5% to about 10%, about 10% to about 15%, about 15% to about 20%. In some embodiments, the concentration of sugar (such as sucrose) by weight, in the aqueous composition, is about any of 1%, 5%, 10%, 15%, 20%. In some embodiments, the concentration of sugar (such as sucrose) by weight, in the aqueous composition, is at most about any of 20%, 15%, 10%, 5%, 1%.

In some embodiments, the sugar is in an amount that is effective to increase the chemical stability of the drug in the composition. In some embodiments, the sugar is in an amount that is effective to improve filterability of the composition. In some embodiments, the sugar is in an amount effective to reduce foaming during reconstitution of the dry (such as lyophilized or frozen) composition. These improvements are as compared to compositions without the sugar.

In some embodiments, the concentration of sugar (such as sucrose) by weight, in the aqueous composition, is between about 5% and about 20%. In some embodiments, the concentration of sucrose by weight, in the aqueous composition, is at least about any of 1%, 5%, 10%, 15%, 20%. In some embodiments, the concentration of sugar (such as sucrose) by weight, in the aqueous composition, is any of about 1% to about 5%, about 5% to about 10%, about 10% to about 15%, about 15% to about 20%. In some embodiments, the concentration of sugar (such as sucrose) by weight, in the aqueous composition, is about any of 1%, 5%, 10%, 15%, 20%. In some embodiments, the concentration of sugar (such as sucrose) by weight, in the aqueous composition, is at most about any of 20%, 15%, 10%, 5%, 1%.

In some embodiments, additional stabilizing excipients may be added to the pre-lyophilized or frozen aqueous composition including amino acids such as monosodium glutamate or histidine; methylamines such as betaine; lyotropic salt such as magnesium sulfate; polyols such as trihydric or higher sugar alcohols, e.g., glycerin, erythritol, glycerol, arabitol, and sorbitol; propylene glycol; Pluronics; and combinations thereof. The excipients are added to the pre-lyophilized or frozen formulation in suitable amounts such that the physical and chemical stability and integrity of the particles are retained upon lyophilization or freezing. In some embodiments, other than PVA and sugar, no other stabilizing excipients are added.

Method of Using the Pharmaceutical Composition

Also provided herein are methods of using the compositions of the present invention. In some embodiments, there is provided a method for treating a disease or condition that is responsive to a drug comprising administering a composition comprising particles comprising a drug and PEG, wherein the particles further comprise PVA, wherein less than about 2% of the total PVA in the pharmaceutical composition is associated with the particles. For example, in some embodiments, there is provided a method of treating cancer in an individual (such as human) comprising administering to the subject a composition comprising an effective amount of a poorly water soluble antineoplastic drug (such as taxane) in PEG-coated particles further comprising PVA, wherein less than about 2% of the total PVA in the pharmaceutical composition is associated with particles. The term "effective amount" used herein refers to an amount of a compound or composition sufficient to treat a specified disorder, condition or disease such as to ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth). In some embodiments, an effective amount is an amount sufficient to delay development. In some embodiments, an effective amount is an amount sufficient to prevent occurrence and/or recurrence. An effective amount can be administered in one or more administrations.

Cancers to be treated by compositions described herein (such as a composition comprising an antineoplastic agent such as taxane, rapamycin, or 17-AAG) include, but are not limited to, carcinoma, lymphoma, blastoma, sarcoma, and leukemia. Examples of cancers that can be treated by compositions described herein include, but are not limited to, squamous cell cancer, lung cancer (including small cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, bladder cancer, glio-blastoma, cervical cancer, ovarian cancer, liver cancer, bladder cancer, heptoma, breast cancer, colon cancer, melanoma, endometrical or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non cleaved cell NHL, bulky disease NHL, mantle cell lymphoma, AIDS-related lymphoma, and Waldenstrom's macroglubulinemia), chronic lymphocytic leukemia (CLL), acute lymphoblastic leukemia (ALL), myeloma, Hairy cell leukemia, chronic myeloblastic leukemia, and post transplant lymphoproliferative disorder (PTLD), as well as abnormal vascular proliferation associated with phakomatoses, edema (such as that associated with brain tumors), and Meigs' syndrome.

In some embodiments, there is provided a method of treating metastatic cancer (that is, cancer that has metastasized from the primary tumor). In some embodiments, there is provided a method of reducing cell proliferation and/or cell migration. In some embodiments, there is provided a method of treating hyperplasia. In some embodiments, there are provided methods of treating cancer at advanced stage(s). In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the cancer is lung cancer, including, for example, non-small cell lung cancer (NSCLC, such as advanced NSCLC), small cell lung cancer (SCLC, such as advanced SCLC), and advanced solid tumor malignancy in the lung. In some embodiments, the cancer is ovarian cancer, head and neck cancer, gastric malignancies, melanoma (including metastatic melanoma), colorectal cancer, pancreatic cancer, and solid tumors (such as advanced solid tumors). In some embodiments, the cancer is any of (and in some embodiments selected from the group consisting of) breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, gliomas, glioblastomas, neuroblastomas, and multiple myeloma. In some embodiments, the cancer is a solid tumor.

An individual suitable for receiving the composition described herein depends on the nature of the drug, as well as the disease/condition/disorder to be treated and/or prevented. Accordingly, the term individual includes any of vertebrates, mammals, and humans. In some embodiments, the individual is a mammal, including, but not limited to, human, bovine, equine, feline, canine, rodent, or primate. In some embodiments, the individual is human.

The compositions described herein can be administered alone or in combination with other pharmaceutical agents, including poorly water soluble pharmaceutical agents. For example, when the composition contains a taxane (such as paclitaxel), it can be co-administered with one or more other chemotherapeutic agents including, but are not limited to, carboplatin, Navelbine® (vinorelbine), anthracycline (Doxil), lapatinib (GW57016), Herceptin, gemcitabine (Gemzar®), capecitabine (Xeloda®), alimta, cisplatin, 5-fluorouracil, epirubicin, cyclophosphamide, avastin, Velcade®, etc. In some embodiments, the taxane composition is co-administered with a chemotherapeutic agent selected from the group consisting of antimetabolites (including nucleoside analogs), platinum-based agents, alkylating agents, tyrosine kinase inhibitors, anthracycline antibiotics, vinca alkloids, proteasome inhibitors, macrolides, and topoisomerase inhibitors. These other pharmaceutical agents can be present in the same composition as the drug (such as taxane), or in a separate composition that is administered simultaneously or sequentially with the drug (such as taxane)-containing composition. Combination therapy methods using particle formulations of taxane with other agents (or therapeutic methods) have been described, for example, in International Patent Application No. PCT/US06/006167, PCT/US09/067766, PCT/US10/027159, and PCI/US11/037450.

The dose of the inventive composition administered to an individual (such as human) will vary with the particular composition, the method of administration, and the particular disease being treated. The dose should be sufficient to effect a desirable response, such as a therapeutic or prophylactic response against a particular disease. For example, the dosage of paclitaxel in the composition can be in the range of 100-400 mg/m$^2$ when given on a 3 week schedule, or 50-250 mg/m$^3$ when given on a weekly schedule. In addition, if given in a metronomic regimen (e.g., daily or a few times per week), the dosage may be in the range of about 5 to about 75 mg/m$^2$, for example any one of about 5 to about 10 mg/m$^2$, about 10 to about 25 mg/m$^2$, about 25 to about 40 mg/m$^2$, about 40 to about 50 mg/m$^2$, about 50 to about 60 mg/m$^2$, about 60 to about 65 mg/m$^2$, about 65 to about 70 mg/m$^2$, about 70 to about 75 mg/m$^2$.

The compositions described herein can be administered to an individual (such as human) via various routes, including, for example, intravenous, intra-arterial, intrapulmonary, oral, inhalation, intravesicular, intramuscular, intra-tracheal, subcutaneous, intraocular, intrathecal, transmucosal, and transdermal. For example, the inventive composition can be administered by inhalation to treat conditions of the respiratory tract. The composition can be used to treat respiratory conditions such as pulmonary fibrosis, broncheolitis obliterans, lung cancer, bronchoalveolar carcinoma, and the like.

In some embodiments, the present invention provides a pharmaceutical composition of PEG-coated particles comprising drugs further comprising PVA, wherein less than about 2% of the total PVA in the pharmaceutical composition is associated with the particles and wherein the pharmaceutical composition is contained in a sealed vial. Also provided are articles of manufacture comprising the compositions described herein in suitable packaging. Suitable packaging for compositions described herein are known in the art, and include, for example, vials (such as seated vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed.

The present invention also provides kits comprising compositions (or unit dosages forms and/or articles of manufacture) described herein and may further comprise instruction(s) on methods of using the composition, such as uses further described herein. In some embodiments, the kit of the invention comprises the packaging described above. In other embodiments, the kit of the invention comprises the packaging described above and a second packaging comprising a buffer. The kits described herein may further include other materials desirable from a commercial and user standpoint, including other buffers, diluents, filters, needles, syringes, and package inserts with instructions for performing any methods described herein.

Kits may also be provided that contain sufficient dosages of the drug (such as paclitaxel) as disclosed herein to provide effective treatment for an individual for an extended period, such as any of a week, 2 weeks, 3 weeks, 4 weeks, 6 weeks, 8 weeks, 3 months, 4 months, 5 months, 6 months, 7 months, 8 months, 9 months or more. Kits may also include multiple unit doses of the drugs and pharmaceutical compositions and instructions for use and packaged in quantities sufficient for storage and use in pharmacies for example, hospital pharmacies and compounding pharmacies.

The following are examples of the methods and compositions of the invention. It is understood that various other embodiments may be practiced, given the general description provided above.

EXAMPLES

Example 1

This example describes the investigation of excipients for the reconstitution of particles after freeze-thaw or lyophilization or freezing. A particle formulation batch was prepared using a water/oil (W/O) emulsion method. Briefly, a 6 ml ethyl acetate/dichloromethane solution was prepared containing 120 mg of PEG-PLGA (5 K: 33 K), 78 mg of PLGA (L:G=85:15), and 9 mg of paclitaxel. The organic mixture was added to 30 ml of an aqueous phase. The mixture was emulsified and then subjected to high pressure homogenization. The organic solvent was then removed. Three batches were prepared using the same formulation composition, pooled together, and filtered. The suspension was washed with cold water and further concentrated to a final volume of 20 ml and placed on ice.

50% (500 mg/ml) sucrose in water was prepared as a stock solution. To this stock solution, various amounts of PVA 75% hydrolyzed (Acros lot #AO 1378570). PVP Povidone K-90 (Spectrum Labs) and PEG 6000 (Hampton Research) were added to yield a 5×concentrated stock solution. 1.33 ml of these stock solutions was added to 2 ml of the particle suspension to produce the desired final excipient concentrations. The particle compositions were lyophilized or frozen. Table 1 provides the results of the freeze-thaw experiments upon addition of various excipients.

The particle suspensions were analyzed using a dynamic light scattering instrument (Zetasizer Nano ZS, Malvern Instruments). The particles that were produced had a $Z_{avg}$ diameter of 137 nm after nitration and before lyophilization or freezing.

The results as shown in Table 1 indicate that even though sucrose and PEG/sucrose used as excipients prevented formation of aggregates or precipitates in the particles suspension, the size of the particles exhibited an increase after a freeze-thaw cycle. Compared to that, use of PVA/sucrose as excipients showed an improved recovery of particles size. The size was nearly identical to the original pre-frozen size of the particles. The recovery was better (136.3 nm compared to 174.1 nm) at lower concentrations of PVA (0.5% compared to 1%). This indicates that there is an optimum concentration of PVA that imparts good freeze-thaw stability for the particles.

TABLE 1

Results from freeze-thaw experiments for screening cryoprotectants.

| Excipients used | $Z_{avg}$ diameter after freeze-thaw | Observations* |
| --- | --- | --- |
| 20% sucrose | 203.5 nm | No instability/aggregates |
| 10% sucrose | 203.5 nm | No instability/aggregates |
| 0.5% PVA + 10% sucrose | 136.3 nm | Some debris |
| 1% PVA + 10% sucrose | 174.1 nm | Debris |
| 0.5% PVP + 10% sucrose | N/A | precipitates |
| 1% PVP + 10% sucrose | N/A | precipitates |
| 3% PEG (6000) + 10% sucrose | 241.5 | No instability/aggregates |

*"Instability" refers to the presence of a precipitate or physical inhomogeneity visible to the unaided eye. "Aggregates" refer to visible or microscopically observable particulates. "Debris" refers to large visible aggregates.

Example 2

This example describes the investigation of different grades of PVA as excipients for reconstitution of particles after lyophilization or freezing. A particle formulation batch was prepared using a water/oil (W/O) emulsion method. Briefly, a 30 ml ethyl acetate/dichloromethane solution was prepared containing 600 mg of PEG-PLGA (L:G=50:50) (5 K:33 K), 390 mg of d, l PLA (80 K), and 45 mg of paclitaxel. The organic mixture was added to 180 ml of an aqueous phase. The mixture was emulsified and then subjected to high pressure homogenization. The organic solvents were then removed. Three batches were prepared using the same formulation composition, pooled together, and filtered. The suspension was washed with cold water and further concentrated to a final volume of 43 ml and placed on ice.

50% sucrose in water was prepared as a 5×stock solution. Stock solutions with various amounts of PVA 75% hydrolyzed (Acros lot#AO1378570), and PVA 15K (MP BioMedical) were prepared to yield a 5×concentrated stock solution of the two PVA's. A 5% PVA stock solution gave a final PVA concentration of 1%, whereas a 1% PVA stock solution gave a final PVA concentration of 0.2%. 0.66 ml of the sucrose stock solution and 0.66 ml of the PVA stock solution each was added to 2 ml of the particle suspension to produce the desired final excipient concentrations. The particles that were produced had a size of 114.3 nm after filtration. Lyophilization was performed in a Genesis 25 EL pilot-scale freeze dryer (SP Industries) using the following freeze-drying cycle described in Table 2.

After lyophilization, the particles were reconstituted using 3 ml of saline. The results and observations are presented in Table 3. These results indicate that using PVA in combination with sucrose improves the reconstitution of particle formulations significantly. With PVA 15K, there is a correlation between PVA concentration and the final size after reconstitution as observed for lyophilized or frozen samples where lower concentrations of PVA resulted in less aggregation. No substantial size change was observed when PVA was added.

TABLE 2

Description of the lyophilization cycle used to investigate excipients (H = hold, R = ramp)

| | Freeze | | | Total |
|---|---|---|---|---|
| Step | Temp (° C.) | Time (min) | R/H | Cycle Time (min) |
| 1 | 25 | 10 | H | 10 |
| 2 | −48 | 70 | R | 80 |
| 3 | −48 | 240 | H | 320 |

| | Primary Drying | | | | Total |
|---|---|---|---|---|---|
| Step | Temp (° C.) | Time (min) | R/H | Vac (mTorr) | Cycle Time (min) |
| 1 | −48 | 30 | H | 50 | 350 |
| 2 | −40 | 15 | R | 50 | 365 |
| 3 | −40 | 1255 | H | 50 | 1620 |
| 4 | −40 | 1255 | H | 50 | 2875 |
| 5 | −40 | 1255 | H | 50 | 4130 |
| 6 | −40 | 1255 | H | 50 | 5385 |
| 7 | −40 | 1255 | H | 50 | 6640 |

| | Secondary Drying | | | | Total |
|---|---|---|---|---|---|
| Step | Temp (° C.) | Time (min) | R/H | Vac (mTorr) | Cycle Time (min) |
| 1 | 5 | 1255 | R | 50 | 7895 |
| 2 | 5 | 240 | H | 50 | 8135 |

TABLE 3

Screening PVA excipients for appropriate lyoprotection at different concentrations in conjunction with 10% sucrose.

| Excipients used | Reconstituted size | Observations* |
|---|---|---|
| 10% sucrose | 143.9 nm | aggregates |
| 0.2% PVA (75% hydrolyzed) + 10% sucrose | 119.5 nm | No instability or aggregates |
| 0.5% PVA (75% hydrolyzed) + 10% sucrose | 118.2 nm | No instability or aggregates |
| 1.0% PVA (75% hydrolyzed) + 10% sucrose | 120.3 nm | Minimal aggregates |
| 0.2% PVA (15K) + 10% sucrose | 123.7 nm | Minimal aggregates |
| 0.5% PVA (15K) + 10% sucrose | 128.1 nm | No instability or aggregates |
| 1.0% PVA (15K) + 10% sucrose | 136.2 nm | No instability or aggregates |

*"Instability" refers to the presence of a precipitate or physical inhomogeneity visible to the unaided eye. "Aggregates" refer to visible or microscopically observable particulates. "Debris" refers to large visible aggregates.

Example 3

This example describes investigation of PVA grades of various molecular weights and sucrose as excipients for particles during lyophilization or freezing. A particle formulation batch was prepared using a water/oil emulsion method. Briefly, a 73 ml ethyl acetate/dichloromethane solution was prepared containing 1.5 g of PEG-PLGA (L:G=50:50) (5K:33K), 0.975 g of d,l,PLA, and 112 mg of paclitaxel. The organic mixture was added to 375 ml of an aqueous phase. The mixture was emulsified and then subjected to high pressure homogenization. The organic solvents were then removed. The final particle solution was brought up to 250 ml using water. The suspension was then filtered. The suspension was washed with cold water and further concentrated 4 times and placed on ice. The particles had a size of 129.8 nm after filtration as measured by the Zetasizer Nano ZS. PVA (85% hydrolyzed) of molecular weights 13,000, 31,000, 85,000 and 124,000 were obtained from Sigma Aldrich. As described in Table 4, PVA was added to the particles solutions at different concentrations along with sucrose at 10% (wt).

TABLE 4

Sample preparation for performing freeze-dry studies using PVA of different molecular weights.
Step 1. Prepare solution A × 50% Sucrose at least 30 ml
Step 2. Prepare solutions of sucrose and various PVA polymers at a concentration of 1% PVA & 60% sucrose B = 1% PVA$_{MW}$ + 50% Sucrose
Step 3. Prepare solutions in different vials in the ratios given in the table below.

| Additive ⇒ | 0.02% PVA$_{MW}$ (5X) | 0.05% PVA$_{MW}$ (5X) | 0.1% PVA$_{MW}$ (5X) | 0.2% PVA$_{MW}$ (5X) |
|---|---|---|---|---|
| 1) PVA (M.W. 13,000) | 4.5 ml A + 0.5 ml B$_{13000}$ | 3.75 ml A + 1.25 ml B$_{13000}$ | 2.6 ml A + 2.5 ml B$_{13000}$ | B$_{13000}$ |
| 2) PVA (M.W. 31,000) | 4.5 ml A + 0.5 ml B$_{31000}$ | 3.75 ml A + 1.25 ml B$_{31000}$ | 2.6 ml A + 2.5 ml B$_{31000}$ | B$_{31000}$ |

TABLE 4-continued

Sample preparation for performing freeze-dry studies using PVA of different molecular weights.
Step 1. Prepare solution A × 50% Sucrose at least 30 ml
Step 2. Prepare solutions of sucrose and various PVA polymers at a concentration of 1% PVA & 60% sucrose B = 1% PVA$_{MW}$ + 50% Sucrose
Step 3. Prepare solutions in different vials in the ratios given in the table below.

| Additive ⇒ | 0.02% PVA$_{MW}$ (5X) | 0.05% PVA$_{MW}$ (5X) | 0.1% PVA$_{MW}$ (5X) | 0.2% PVA$_{MW}$ (5X) |
|---|---|---|---|---|
| 3) PVA (M.W. 85,000) | 4.5 ml A + 0.5 ml B$_{85000}$ | 3.75 ml A + 1.25 ml B$_{85000}$ | 2.6 ml A + 2.5 ml B$_{85000}$ | B$_{85000}$ |
| 4) PVA (M.W. 124,000) | 4.5 ml A + 0.5 ml B$_{124000}$ | 3.75 ml A + 1.25 ml B$_{124000}$ | 2.6 ml A + 2.5 ml B$_{124000}$ | B$_{124000}$ |

After the particle solutions were prepared with the addition of PVA/sucrose, the vials were placed in a Genesis 25EL lyophilizer and subjected to the lyophilization or freezing cycle described in the Table 2. The particles were dried to a powder form after the lyophilization or freezing cycle was completed. To study the reconstitution of the dried particles, 2.5 ml of DI water was gently added to each vial and the particles were allowed to equilibrate for 5 minutes before further analyses. Upon reconstitution, the particle suspensions were analyzed using the Zetasizer NanoZS. The results obtained are presented in Table 5.

It was observed that all vials lyophilized using PVA 85K and 124K as an excipient reconstituted poorly with aggregates visible to the eye. Vials lyophilized using PVA 13K and 31K at a concentration of 0.1 and 0.2% (wt) reconstituted well with no visible particulates or microscopically observable aggregates.

It was also observed that the vials lyophilized using PVA 13K and 31K at a concentration of 0.1 and 0.2% (wt) reconstituted to a particle size measured by the Zetasizer Nano ZS not more than 10% larger than the particle size measured in the suspension prior to lyophilization. In the case where PVA 13K was added at a concentration of 0.2% (wt), the particle size increased by less than 4% over the pre-lyophized size.

TABLE 5

Reconstituted $Z_{avg}$ particle diameter obtained for PVA of different molecular weights when used as excipients in conjunction with 10% sucrose during a freeze-dry cycle. The values in parenthesis represent the corresponding polydispersity index of the particle size distribution.

| Additive » | 0.02% | 0.05% | 0.10% | 0.20% |
|---|---|---|---|---|
| PVA$_{13K}$ | 161.4 (0.230) | 145.2 (0.260) | 138.6 (0.255) | 133.6 (0.224) |
| PVA$_{31K}$ | 138.2 (0.228) | 142.3 (0.257) | 143.1 (0.260) | 136.3 (0.236) |
| PVA$_{85K}$ | 143.4 (0.267) | 145.8 (0.262) | 155.9 (0.283) | 155.1 (0.287) |
| PVA$_{124K}$ | 141.3 (0.226) | 147.9 (0.271) | 174.0 (0.243) | 189.9 (0.342) |

Although the foregoing invention has been described in some detail by way of illustration and example for purposes of clarity of understanding, the descriptions and examples should not be construed as limiting the scope of the invention.

What is claimed is:

1. A method of preparing a lyophilized or frozen preparation of a composition comprising particles comprising a drug, wherein the particles are liposomes or micelles, and wherein the particles are coated with polyethylene glycol (PEG), the method comprising adding polyvinyl alcohol (PVA) to an aqueous composition comprising the particles, and lyophilizing or freezing the aqueous composition.

2. A method of preventing particle aggregation and/or particle size increase upon lyophilization and resuspension or freezing and thawing of an aqueous composition comprising particles comprising a drug, wherein the particles are liposomes or micelles, and wherein the particles are coated with polyethylene glycol (PEG), the method comprising adding polyvinyl alcohol (PVA) to the aqueous particle composition prior to lyophilization or freezing.

3. The method of claim 1, wherein the concentration of PVA in the aqueous particle composition is between about 0.05% (w/v) to about 1% (w/v).

4. The method of claim 3, wherein the concentration of PVA in the aqueous particle composition is about 0.1 to about 0.3%.

5. The method of claim 1, wherein the PVA is about 3K to about 125K.

6. The method of claim 5, wherein the PVA is about 13K or about 31K.

7. The method of claim 1, wherein the PVA is at least about 50% hydrolyzed.

8. The method of claim 7, wherein the PVA is at least about 75% hydrolyzed.

9. The method claim 1, wherein the weight ratio of the PVA to the particles in the resultant composition is less than about 0.2:1.

10. The method of claim 1, wherein the concentration of the particles in the aqueous particle composition is about 1% to about 25% (w/v).

11. The method of claim 1, wherein the particles comprise PLA or PLGA.

12. The method of claim 1, wherein the average particle size of the particles in the particle composition is no greater than about 200 nm.

13. The method of claim 1, wherein the average size of the particles does not change by more than about 10% upon lyophilization and resuspension or freezing and thawing.

14. The method of claim 1, further comprising adding a sugar to the aqueous particle composition prior to lyophilization or freezing.

15. The method of claim 14, wherein the sugar is sucrose.

16. The method of claim 15, wherein the concentration of sucrose in the aqueous particle composition is between about 5% to about 20%.

17. The method of claim 14, wherein the sugar and the PVA are added simultaneously or sequentially into the particle composition.

18. The method of claim 1, wherein the aqueous particle composition to which the PVA is added is free of PVA.

19. The method of claim 1, wherein the PEG is covalently attached to the surface of the particles or tethered to the surface of the particles by hydrophobic or charge interactions.

20. The method of claim 1, wherein the drug is paclitaxel.

21. A pharmaceutical composition comprising particles comprising a drug, wherein the particles are liposomes or micelles, and wherein the particles are coated with polyethylene glycol (PEG), wherein the composition further comprises polyvinyl alcohol (PVA), and wherein less than about 2% of the total PVA in the pharmaceutical composition is associated with the particles.

22. The pharmaceutical composition of claim 21, wherein the composition is lyophilized or frozen.

23. The pharmaceutical composition of claim 21, wherein the composition is an aqueous suspension resuspended from a lyophilized or frozen composition.

24. The pharmaceutical composition of claim 21, wherein the composition is an aqueous suspension.

25. The pharmaceutical composition of claim 21, wherein the concentration of PVA in the particle composition is between about 0.05% to about 1%.

26. The pharmaceutical composition of claim 25, wherein the concentration of PVA in the particle composition is about 0.1% to about 0.3%.

27. The pharmaceutical composition of claim 21, wherein the PVA is about 3K to about 125K.

28. The pharmaceutical composition of claim 27, wherein the PVA is about 13K or about 31K.

29. The pharmaceutical composition of claim 21, wherein the PVA is at least about 50% hydrolyzed.

30. The pharmaceutical composition of claim 29, wherein the PVA is at least about 75% hydrolyzed.

31. The pharmaceutical composition of claim 21, wherein the particles comprise a polymeric matrix core coated with PEG.

32. The pharmaceutical composition of claim 31, wherein the particles comprise PLA or PLGA.

33. The pharmaceutical composition of claim 21, wherein the average particle size of the particles in the particle composition is no greater than about 200 nm.

34. The pharmaceutical composition of claim 21, further comprising a sugar.

35. The pharmaceutical composition of claim 34, wherein the sugar is sucrose.

36. The pharmaceutical composition of claim 35, wherein the concentration of sucrose in the particle composition is between about 5% to about 20%.

37. The pharmaceutical composition of claim 21, wherein the PEG is covalently attached to the surface of the particles or tethered to the surface of the particles by hydrophobic or charge interactions.

38. The pharmaceutical composition of claim 21, wherein the weight ratio of the PVA to the particles in the composition is less than about 0.2:1.

39. The pharmaceutical composition of claim 21, wherein the concentration of the particles in the aqueous particle composition is about 1% to about 25% (w/v).

40. The pharmaceutical composition of claim 21, wherein the pharmaceutical composition is contained in sealed vial.

41. A pharmaceutical composition produced by the method of claim 1.

42. The pharmaceutical composition of claim 21, wherein the drug is paclitaxel.

43. The method of claim 1, wherein the particles are liposomes.

44. The method of claim 1, wherein the particles are micelles.

45. The pharmaceutical composition of claim 21, wherein the particles are liposomes.

46. The pharmaceutical composition of claim 21, wherein the particles are micelles.

* * * * *